(12) United States Patent
Escribá Ruiz et al.

(10) Patent No.: US 9,359,281 B2
(45) Date of Patent: Jun. 7, 2016

(54) ENANTIOMERS OF 2-HYDROXY DERIVATIVES OF FATTY ACIDS

(71) Applicants: Pablo Vicente Escribá Ruiz, Palma de Mallorca (ES); María Laura Martín, Palma de Mallorca (ES); María Antònia Noguera Salvà, Palma de Mallorca (ES); Xavier Busquets Xaubet, Palma de Mallorca (ES); David López Jiménez, Palma de Mallorca (ES); Maitane Ibarguren Aizpitarte, Palma de Mallorca (ES); José Javier Soto Salvador, Alicante (ES); Miguel Yus Astiz, Alicante (ES)

(72) Inventors: Pablo Vicente Escribá Ruiz, Palma de Mallorca (ES); María Laura Martín, Palma de Mallorca (ES); María Antònia Noguera Salvà, Palma de Mallorca (ES); Xavier Busquets Xaubet, Palma de Mallorca (ES); David López Jiménez, Palma de Mallorca (ES); Maitane Ibarguren Aizpitarte, Palma de Mallorca (ES); José Javier Soto Salvador, Alicante (ES); Miguel Yus Astiz, Alicante (ES)

(73) Assignee: UNIVERSITAT DE LES ILLES BALEARS, Palma de Mallorca (ES)

( * ) Notice: Subject to any disclaimer, the term of this patent is extended or adjusted under 35 U.S.C. 154(b) by 126 days.

(21) Appl. No.: 14/349,962

(22) PCT Filed: Oct. 8, 2012

(86) PCT No.: PCT/ES2012/070697
§ 371 (c)(1),
(2) Date: Apr. 4, 2014

(87) PCT Pub. No.: WO2013/050644
PCT Pub. Date: Apr. 11, 2013

(65) Prior Publication Data
US 2014/0288176 A1   Sep. 25, 2014

Related U.S. Application Data

(60) Provisional application No. 61/610,762, filed on Mar. 14, 2012.

(30) Foreign Application Priority Data

Oct. 7, 2011   (ES) .................................. 201131622

(51) Int. Cl.
*A61K 31/20* (2006.01)
*C07C 59/42* (2006.01)
*C07C 51/493* (2006.01)

(52) U.S. Cl.
CPC .............. *C07C 59/42* (2013.01); *C07C 51/493* (2013.01); *C07B 2200/07* (2013.01)

(58) Field of Classification Search
CPC .............................. A61K 31/20; C07C 59/42
USPC .......................................... 514/560; 554/219
See application file for complete search history.

(56) References Cited

U.S. PATENT DOCUMENTS

2011/0294883 A1   12/2011   Escribá Ruiz et al.
2012/0108550 A1   5/2012    Escriba Ruiz et al.

FOREIGN PATENT DOCUMENTS

WO   2010066931 A1   6/2010
WO   2010106211 A1   9/2010

OTHER PUBLICATIONS

Albi, E. and M. V. Magni (1999). Sphingomyelin synthase in rat liver nuclear membrane and chromatin. FEBS Letters 460: 369-72.
Alemany R, Terés S, Baamonde C, Benet M, Vögler O, Escribá PV. (2004) 2-hydroxyoleic acid: a new hypotensive molecule. Hypertension. 43: 249-54.
Alemany R, Perona JS, Sánchez-Domínguez JM, Montero E, Cañizares J, Brezan R, Escribá PV and Ruiz-Gutiérrez V (2007) G protein-coupled receptor systems and their lipid environment in health disorders during aging. BBA Biomembr. 1768:964-975.
Buda C, Dey I, Balogh N, Horvath LI, Maderspach K, Juhasz M, Yeo YK, Farkas T (1994) Structural order of membranes and composition of phospholipids in fish brain cells during thermal acclimatization. Proc. Natl. Acad. Sci USA 91:8234-8238.
Escribá PV, Sastre M, Garcia-Sevilla JA. (1995) Disruption of cellular signaling pathways by daunomycin through destabilization of nonlamellar membrane structures. Proc Natl Acad Sci U S A. 92:7595-7599.
Escribá PV, Ozaita A, Ribas C, Miralles A, Fodor E, Farkas T, Garcia-Sevilla JA (1997) Role of lipid polymorphism in G protein-membrane interactions: nonlamellar-prone phospholipids and peripheral protein binding to membranes. Proc Natl Acad Sci U S A. 94:11375-11380.
Escribá PV (2006) Membrane-lipid therapy: a new approach in molecular medicine. Trends Mol. Med. 12:34-43.
Escribá PV, González-Ros JM, Goñi FM, Kinnunen PKJ, Vigil L, Sánchez-Magraner L, Fernández AM, Busquets X, Horváth I, Barceló-Coblijn G (2008) Membranes: A meeting point for lipids, proteins and therapies. J Cell. Mol. Med. 12:829-875.

(Continued)

*Primary Examiner* — Raymond Henley, III
(74) *Attorney, Agent, or Firm* — Tristan A. Fuierer; Moore & Van Allen, PLLC

(57) ABSTRACT

This invention refers to the synthesis and purification of 2 hydroxide derivatives of fatty acids, as well as to the separation method of its enantiomers (or optic isomers) [−] y [+], to the enantiomers themselves, to pharmaceutical compositions which include them, and to their use as medicines, as well as to an in vitro method of diagnosis/prognosis and evaluation of the potential use of the molecules of the invention in different pathologies, as well as their use for the regulation of certain enzymes and the study of their activity and effects.

10 Claims, 17 Drawing Sheets

(56) References Cited

OTHER PUBLICATIONS

Figure 1:
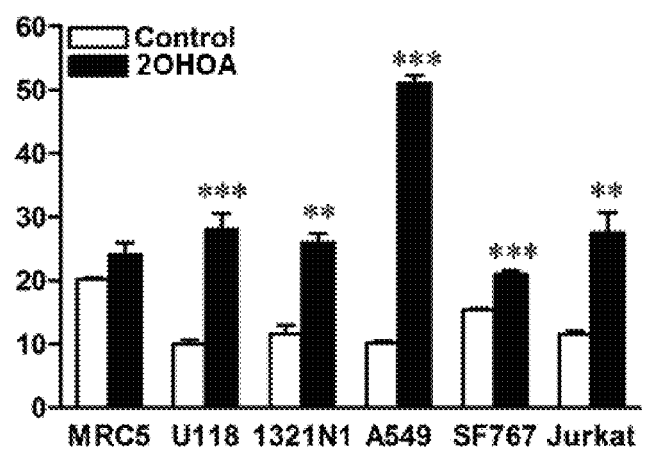
Figure 1:
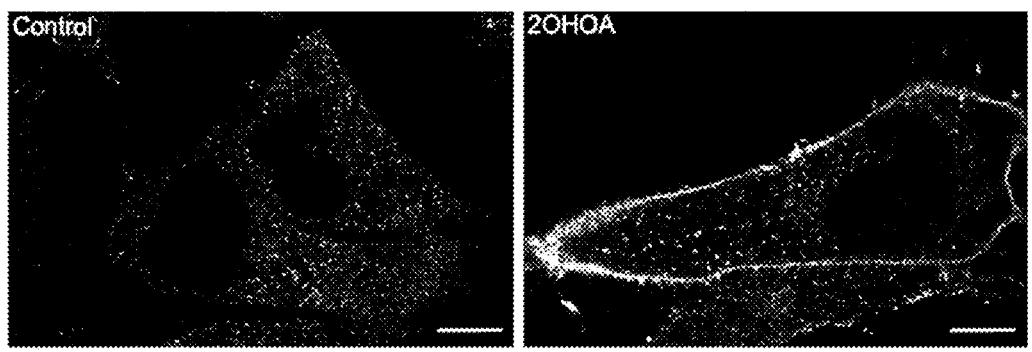
Figure 1:
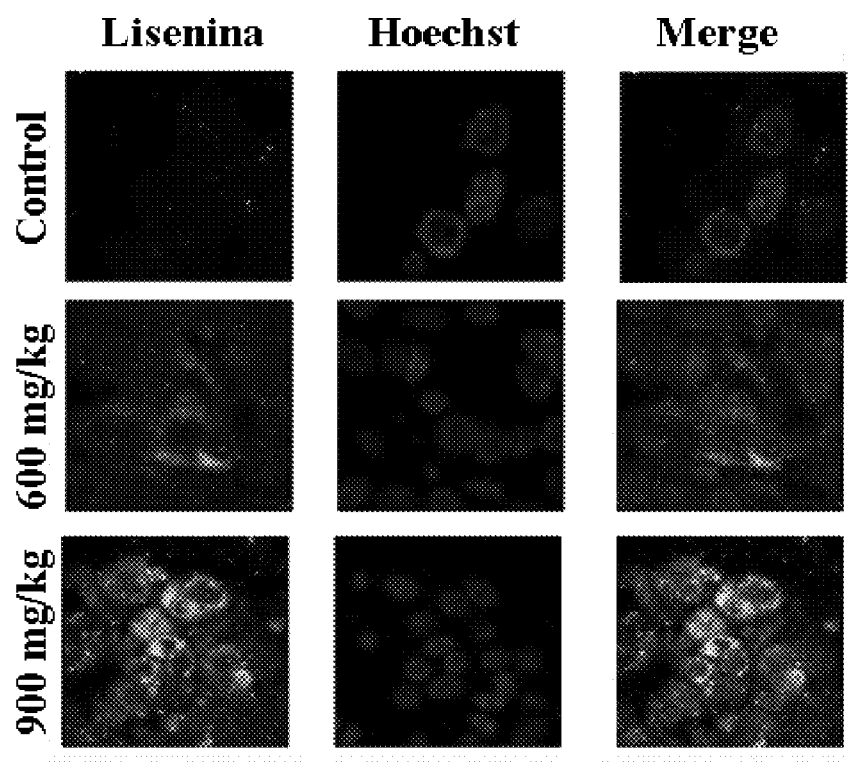
Figure 1:
Figure 1:
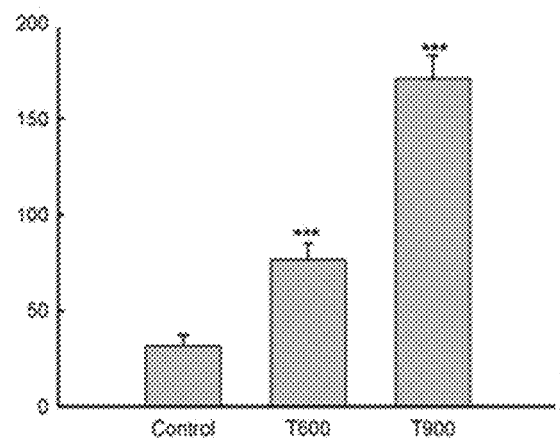
Figure 1:
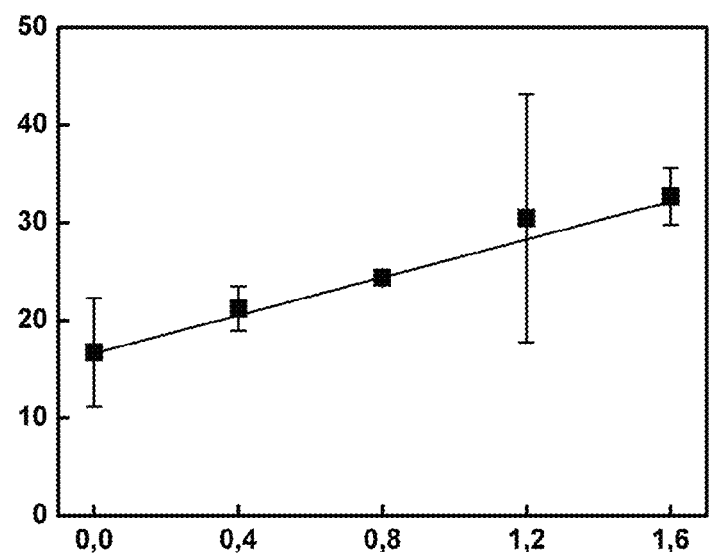

Florent S, Malaplate-Armand C, Youssef I, Kriem B, Koziel V, Escanyé MC, Fifre A, Sponne I, Leininger-Muller B, Olivier JL, Pillot T, Oster T. (2006) Docosahexanoic acid prevents neuronal apoptosis induceed by soluble amyloid-beta oligomers. J Neurochem. 96:385-95.

Huitema, K., et al. (2004). Identification of a family of animal sphingomyelin synthases. EMBO J 23:33-44.

Jackson CL, Schwartz SM (1992) Pharmacology of smooth muscle cell replication. Hypertension 20: 713-736.

Jiang Q, et al. (2011). Gamma-tocotrienol induces apoptosis and autophagy in prostate cancer cells by increasing intracellular dihydrosphingosine and dihydroceramide. Int J Cancer. doi: 10.1002/ijc.26054.

Jung UJ, Torrejon C, Tighe AP, Deckelbaum RJ. (2008). N-3 Fatty acids and cardiovascular disease mechanisms underlying beneficial effects. Am J Clin Nutr. 87:2003S-2009S.

Lane RM, Farlow MR.(2005) Lipid homeostasis and apolipoprotein E in the development and progression of Alzheimer's disease. J Lipid Res. 46: 949-968.

Lladó V, Gutierrez A, Martinez J, et al. Minerval induces apoptosis in Jurkat and other cancer cells. J. Cell Mol Med. 2010; vol. 14, No. 3: 659-670.

Martínez J, 0, Casas J, F, Alemany R, Prades J, Nagy T, Baamonde C, Kasprzyk P, Terés S, Saus C, Escribá PV. (2005) Membrane structure modulation, protein kinase C alpha activation, and anticancer activity of minerval. Mol Pharmacol 67:531-40.

Perona JS, Vögler O, Sánchez-Domínguez JM, Montero E, Escribá PV and Ruiz-Gutierrez EV (2007) Consumption of virgin olive oil influences membrane lipid composition and regulates intracellular signaling in elderly adults with type 2 diabetes mellitus. J. Gerontol A Biol Sci Med Sci 62: 256-263.

Sagin FG, Sozmen EY (2008) Lipids as key players in Alzheimer disease: alterations in metabolism and genetics. Curr Alzheimer Res 5:4-14.

Simons, K. and D. Toomre (2000). Lipid rafts and signal transduction. Nat Rev Mol Cell Biol 1:31-9.

Sloan, F.A., Bethel, M. A, Ruiz, D. Jr., Shea, A. M & Feinglos, M. N. The growing burden of diabetes mellitus in the US elderly population. Arch. Intern. Med. 168, 192-199 (2008).

Slomiany A, Murty VL, Aono M, Snyder CE, Herp A and Slomiany BL (1982) Lipid composition of tracheobronchial secretions from normal individuals and patients with cystic fibrosis. Biochim Biophys Acta. 710:106-111 D.

Stender S, Dyerberg J (2004) Influence of trans fatty acids on health. Ann. Nutr. Metab. 48:61-66.

Schwartz SM, Campbell GR, Campbell JH. (1986). Replication of smooth muscle cells in vascular disease. Circ Res 58:427-444.

Tafesse, F. G., P. Ternes, et al. (2006). The multigenic sphingomyelin synthase family. J Biol Chem 281: 29421-5.

Trombetta A, Maggiora M, Martinasso G, Cotogni P, Canuto RA, Muzio G. (2007). Arachidonic and docosahexanoic acids reduce the growth of A549 human lung tumor cells increasing lipid peroxidation and PPARs. Chem Biol Interact. 165:239-50.

Van Helvoort, A., W. van't Hof, et al. (1994). Conversion of diacylglycerol to phosphatidylcholine on the basolateral surface of epithelial (Madin-Darby canine kidney) cells. Evidence for the reverse action of a sphingomyelin synthase. J Biol Chem 269: 1763-9.

Vögler O, Casas J, Capó, D, Nagy T, Borchert G, Martorell G and Escribá. PV. (2004) The Gbetagamma dimer drives the interaction of heterotrimeric Gi proteins with nonlamellar membrane structures. J Biol Chem. 279:36540-36545.

Vögler O, López-Bellan A, Alemany R, Tofé S, González M, Quevedo J, Pereg V, Barceló F and Escribá PV.(2008) Structure-effect relation of C18 long-chain fatty acids in the reduction of body weight in rats. Int J Obes. 32: 464-473.

Wise LE, Iredale PA, Stokes RJ, Litchman AH (2007) Combination of Rimonabant and Donepezil prolongs spatial memoryduration. Neuropsychopharmacology 32: 1805-1812.

Yang, Q, Alemany, R, Casas, J, Kitajka, K, Lanier, SM, Escribá PV (2005) Influence of the membrane lipid structure on signal processing via G protein coupled receptors. Mol Pharmacol 68:210-7.

Registry database, CAS (Chemical Abstracts Service) in STN. Compounds bearing Registry No. 214204-40-7 (date of entry in CAS Nov. 12, 1998) and 182370-45-2 (date of entry in CAS Oct. 29, 1996).

Diario El Mundo Baleares, Apr. 21, 2009. Sección Investigación. "Minerval, la molécula victoriosa" & retrieved from the Internet, http://www.elmundo.es/elmundo/baleares.html, the entire document, Apr. 21, 2009.

W Adam et al., European Journal Organic Chemistry 1998, pp. 2013-2018. "Synthesis of optically active alfa-hydroxyacids by kinetic resolution through lipase-catalyzed enantioselective acetylacion", the entire document, 1998.

M R Hojjati et al., Journal of Lipid Research 2006, vol. 47, pp. 673-676. "Rapid, specific and sensitive measurments of plasma sphingomyelin and phosphatidylcholine", abstract, 2006.

International Search Report, Dec. 5, 2012.

A)

B)

C)

Upper panels

Central panels

C)

Bottom Panels

D)

A)

B)

C)

A)

B)

A)

B)

A)

B)

E)

ENANTIOMERS OF 2-HYDROXY DERIVATIVES OF FATTY ACIDS

CROSS-REFERENCE TO RELATED APPLICATIONS

This application is filed under the provisions of 35 U.S.C. §371 and claims the priority of International Patent Application No. PCT/ES2012/070697 filed on 8 Oct. 2012 entitled "ENANTIOMERS OF 2-HYDROXY DERIVATIVES OF FATTY ACIDS" in the name of Pablo Vicente ESCRIBÁ RUIZ, et al, which claims priority to U.S. Provisional Patent Application No. 61/610,762 filed on Mar. 14, 2012, and Spanish Patent Application No. 201131622, filed on 7 Oct. 2011, all of which are hereby incorporated by reference herein in their entirety.

FIELD OF INVENTION

This invention refers to a method for synthesising racemic products and separating their optic isomers [−] (which corresponds to enantiomer S) and [+] (which corresponds to enantiomer R) of 2 hydroxide compound derivatives of fatty acids, isolated enantiomers themselves, their pharmaceutical components, and their medical uses for treating diseases whose common etiology is based on changes (whatever their origin) in the lipids of the cell membrane such as, for example: changes in the level, composition, or structure of said lipids, and also in the treatment of diseases in which regulating the composition and structure of lipids in the membrane can induce a reversion of the pathology. The therapeutic effect is achieved, preferably, by regulating (activating or inhibiting) the activity of the ceramide: phosphocholine cholinephosphotransferase enzyme (EC 2.7.8.27, *IUBMB Enzyme Nomenclature*) or of levels of its product, sphingomyelin (SM). As a result of the activity of this enzyme and of the SM production and its accumulation in the membrane, in the tumour cell, an increase (up to 600% increase) of the Glial fibrillary acidic protein (GFAP) and a reduction (more than 90%) of enzyme Dihydrofolate reductase (DHFR) levels are produced. Therefore, both GFAP and DHFR can be used for the screening of drugs therapeutically effective for the treatment of diseases mediated by the sphingomyelin synthase activity or by SM itself. The present invention also refers to the development of a kit for the detection of said diseases.

In addition, both the enzyme EC 2.7.8.27 and the sphingomyelin (SM) may be used as molecular markers of the effect of the compounds of present invention for the aforementioned diseases. Thus, this invention also includes an in vitro method for the diagnosis/prognosis of these diseases based on the activity of enzyme EC 2.7.8.27 and/or the level of SM, GFAP or DHFR, as well as a kit comprising means specially designed for carrying out the diagnosis/prognosis. These methods and kits will be based in the determination of changes induced by treatment with molecules mentioned herein or in the possibility of changing the abovementioned molecular entities with said treatments.

Furthermore, enzyme EC 2.7.8.27 and/or the level of SM may be used as therapeutic targets to which we can direct molecules that are able to revert alterations and thus treat any pathological processes which have developed or are about to develop in the future as a result of abnormal activity of enzyme EC 2.7.8.27 or of abnormal levels of SM. In this way, both enzyme EC 2.7.8.27 and SM itself can be used as the basis for designing screening selection processes for possible compounds in order to obtain molecules like the enantiomers [−] (also known as S) and [+] (corresponding to form R) of 2-hydroxide derivative of fatty acids of the invention, which are able to regulate the activity of enzyme EC 2.7.8.27 and/or the level of SM, with therapeutic effects.

Thus, due to its wide spectrum of applications, this invention may be included in the fields of medicine and pharmacy in general. It is important to point out that pharmaceutical regulatory agencies require the existence of methods or kits for monitoring the effectiveness of a compound with a certain therapeutic activity, so the description of said compound, its synthesis, its therapeutic scope and its detection should be considered part of this invention.

PRIOR ART

Cell membranes are structures which define the entity of the cells and of the organelles inside them. Most biological processes take place in the cells or near them. Lipids not only play a structural role, they also regulate activity in several important processes. Moreover, regulating the lipid composition of the membrane also affects the location and function of important proteins involved in the control of cellular physiology, such as protein G or PKC (Escribá et al., 1995; Escribá et al., 1997; Yang et al., 2005; Martínez et al., 2005). These studies and others show the importance of lipids for controlling important cell functions. In fact, many human diseases such as cancer, cardiovascular diseases, neurodegenerative processes, obesity, metabolic disorders, swelling, infectious and autoimmune diseases (among others) have been related to changes in the levels or composition of lipids present in biological membranes, and at the same time the beneficial effects of treatments with fatty acids—different from those presented in this invention—which regulate the composition and structure of membrane lipids have been proved. They can be use to reverse these diseases (Escribá et al., 2006). The lipids which we take in with our diet regulate the lipid composition of cell membranes (Alemany et al., 2007). At the same time, different physiological and pathological circumstances may change the lipids present in the cell membranes (Buda et al., 1994; Escribá et al., 2006). Changes in the lipid composition of the membranes can affect cellular signalling, giving rise to diseases or reversing them (Escribá et al., 2006).

Different studies over recent years show that lipids in the membrane play a much more important part than had previously been assigned to them (Escribá et al., 2008). One example of this important role is provided by fish which live in rivers with a varying temperature: their lipids undergo important changes (in quantity and types of lipid in the membrane) when temperatures fall from 20° C. in the summer to 4° C. in the winter (Buda et al., 1994). These changes enable them to maintain functions in very diverse cell types. We can, for this reason, affirm that the lipids in the membrane can determine the correct or incorrect functioning of numerous mechanisms of cellular signalling. Given that a diseased organism is diseased because its cells are, changes in membrane lipids can give rise to diseases. In the same way, therapeutic, nutraceutic, or cosmetic formulations which focus on regulating membrane lipid levels can prevent and revert (cure) pathological processes. Furthermore, many studies show that the intake of saturated fats and trans-monounsaturates is connected to loss of health. Vascular diseases and tumours, among others, are directly connected to this type of lipids (Stender et al., 2004). An organism's deterioration may be seen in the appearance of these and other types of illness.

Cell membranes are the selective barrier through which a cell exchanges metabolites and information with other cells and with its external surroundings. However, membranes have other important cellular functions. On the one hand, they act as a support for proteins involved in the reception and transmission of messages which control important organic parameters. These messages activate, via many hormones, neurotransmitters, cytoquines, growth factors, etc., the proteins in the membrane which propagate the received signal via other proteins, some of which are also contained in the membrane. Given that (1) these systems function as cascades of amplification and that (2) membrane lipids can regulate the location and function of the aforesaid proteins, the lipid composition of the membranes can have a significant impact on cell function. In fact, the interaction between certain proteins (known as peripherals, like G proteins, kinase C protein, Ras protein, etc) and the membrane depends on the lipid composition the same (Vögler et al., 2004; Vögler et al., 2008). On the other hand, the lipid composition of the membranes is influenced by the kind and quantity of lipids ingested (Perona et al., 2007). from this we can deduce that the intake of lipids can regulate the lipid composition of the membranes, and this in turn can control the interaction (and therefore the activity) of important proteins for cell signalling (Yang et al., 2005).

The fact that membrane lipids can control cell signalling suggests that they can also regulate the physiological state of the cells. In fact both positive and negative effects of lipids on health have been documented (Escribá et al., 2006; Escribá et al., 2008). Preliminary studies have shown that 2-hydroxy-oleic acid, which is a monounsaturated fatty acid, is able to reverse certain pathological states such as overweight, hypertension and cancer (Alemany et al., 2004; Martínez et al., 2005; Vögler et al., 2008).

Cardiovascular diseases are frequently linked to the hyper-proliferation of the cells which make up cardiac and vascular tissue. This hyper-proliferation of the cardiovascular cells gives rise to deposits on the internal lumen of the vessels and cavities of the cardiovascular system which cause a wide range of diseases such as hypertension, arteriosclerosis, ischemia, heart attacks, etc. (Schwartz et al., 1985). The development of medication to avoid cell proliferation has, in fact, been proposed to prevent and treat cardiovascular diseases (Jackson et al., 1992).

Obesity or overweight are the result of a change in the balance between energy ingestion and use, partly due to alterations in the mechanisms which regulate these processes. On the other hand, this pathology is typified by hyperplasia (an increase in the number of cells) or hypertrophy (an increase in their size) of the cells of adipose tissue, the adipocites. Many studies show that fatty acids, both free radicals or as a part of other molecules, can affect a series of parameters related to energetic homeostasis, such as the mass of body fat, lipid metabolism, thermogenesis, or ingestion, among others (Vögler et al., 2008). In this sense, modifying fatty acids could be a strategy for regulating energetic homeostasis and, thus, body weight. In fact, this invention shows how low levels of SM in cells are linked to incremented cell proliferation and that this change is linked to the pathological state of human cells. Furthermore, regulating enzyme EC 2.7.8.27 via the molecules described in this invention can normalise SM levels in pathological cells and so reverse the patho-physiological alterations here described. In the context of metabolic pathologies, apart from obesity, lipid intake also determines the appearing of other pathological processes, such as hypercholesterolemia and hypertriglyceridemia, diabetes or metabolic syndrome (Sloan et al., 2008).

Neurodegenerative processes give rise to a series of diseases with different symptoms, but with the common factor that they are caused by the degeneration of the central and/or peripheral nervous system. Some of these neurodegenerative processes mean a significant drop in the cognitive capacity of patients, as in Alzheimer's or senile dementia. Others cause changes to the motor cells, as in Parkinson's disease or different types of sclerosis. Finally, certain neurodegenerative diseases can lead to processes which result in blindness, hearing problems, disorientation, mood swings, etc.

One example of a well-typified neurodegenerative disorder is Alzheimer's disease, where we can observe the formation of senile plaques made up of the remains of incorrectly processed membrane proteins (such as peptide β-amyloid), which build up on the exterior of cells, and of balls of neurofilaments of Tau protein which appear inside the cell. This process has been linked to changes in the metabolism of cholesterol and the resulting change in levels of cholesterol in cell membranes (Sagin et al., 2008). In fact, the development of this disease is linked to other diseases in which changes to lipid metabolism have been observed, more specifically, cholesterol, as in cardiovascular cases.

Apart from this, sclerosis and other neurodegenerative processes are linked to "dismyelinisation", the net result of which is the loss of lipids from the shell of neuronal axons, leading to changes in the process of propagating electrical signals. Myelin is a lipid layer around the axons of many neurones and is formed by a series of spiraling folds in the plasmatic membrane of cells in the glia (Schwann's cells). Because of all this, it is clear that lipids play a very important part in the development of neurodegenerative diseases. Moreover, it has been shown that unmodified natural polyunsaturated fatty acids have a moderate preventative effect on neurodegenerative processes (Lane et al., 2005).

Metabolic diseases make up a group of pathologies typified by the build-up or lack of certain molecules. A typical example is the build-up of cholesterol and/or triglycerides above normal levels. The increase in the level cholesterol and/or triglycerides, both systemic (for example, an increase in plasmatic levels) and cellular (for example, in cell membranes), are linked to changes in the signalling which lead to dysfunctions at several levels, and which are usually due to errors in the activity of certain enzymes or the control of said proteins. Among the main metabolic pathologies are hypercholesterolemia (high levels of cholesterol) and hypertriglyceridemia (high levels of triglycerides). These diseases have high rates of incidence, morbidity and mortality, so their treatment is first priority. Furthermore, ingested lipids can determine the apparition of diabetes (Sloan et al., 2008).

The protective role of certain unsaturated fatty acids for certain diseases has already been documented by different researchers. Thus, unsaturated fatty acids slow down the development of cancer and have beneficial effects against the development of cardiovascular diseases, neurodegenerative pathologies, metabolism, obesity, swelling, etc. (Trombetta et al., 2007; Jung et al., 2008; (Florent et al., 2006). However, the pharmacological activity of these compounds is very limited due to their rapid metabolisation and short half-lives in the blood. It is therefore necessary to develop unsaturated fatty acids with a slower metabolism, resulting in an increase of them in the cell membrane compared with the unsaturated fatty acids used so far, and to facilitate the interaction between peripheral proteins for cell signalling. Molecules described in the present specification meet the structural characteristics which determine a positive effect on health of certain natural fatty acids, together with molecular modifications which enhance the effect of original molecules and, in addition, prevent its quick hydrolysis (metabolism), being both features essential for determining its pharmacological activity.

Digging deeper into the importance of the lipids in the cell membrane, sphingolipids or sphingophospholipids are an important class of lipids in the cell membrane and the most abundant in the tissues of more complex organisms. The molecules of sphingolipids present amphipatic properties, i.e. both hydrophobic and hydrophilic, which enables them to carry out an important task in the formation of biological membranes. Some of the glucosphingolipids are found on the surface of red blood cells and in other cells, acting as antigens and establishing blood groups.

Sphingolipids, then, are very important biologically because of their role in cellular signalling. To be exact, SM is a type of sphingolipid which abounds in the cell membrane of all organisms (Huitema et al., 2004). It is mainly found in the external mono-layer of the plasmatic membrane, where it has an essential function in the forming of micro-domains known as lipid rafts, which are specialised parts of the cell membrane with an important role in cell signalling, as these domains concentrate proteins which interact thanks to the approximation that derives from their union to lipids (Simons y Toomre, 2000). Enzyme EC 2.7.8.27 is responsible for the synthesis of SM via the transferral of a phoshocholine to the primary hydroxyle group of the ceramide to form the SM and 1,2-diacilglicerol (DAG). This enzyme occupies a central position in the metabolism of sphingolipids and glycerophospholipids. EC 2.7.8.27 is found in the plasmatic membrane, in Golgi's apparatus, and its activity has also been detected in the nuclear membrane and in chromatine (Albi et al., 1999). EC 2.7.8.27 also regulates levels of ceramides and diacylglycerol (DAG), both of these molecules being in turn responsible for programmed cell death by apoptosis and autophagy (Jiang et al., 2011; Van Helvoort et al., 1994; Tafesse et al., 2006). The polar head of the SM is very large and impedes the attaching of proteins like Ras, which have ramified lipids (like the remains: isoprenyl, farsenyl or geranilgeranyl), but favours the attaching of other proteins with the remains of saturated fatty acids (like myristic or palmitic acids).

So, given the importance of enzyme EC 2.7.8.27 and of SM to the correct functioning and structure of the cell membrane, and knowing the connection between structural and function changes of the lipids in the cell membrane with the onset of several diseases such as cancer, cardiovascular diseases, obesity, neurodegenerative and metabolic disorders, it is important to find compounds capable of regulating the activity of this enzyme and, as a result, the level of SM, so as to be able to reverse pathologies whose origins are due to abnormal activity of the enzyme and/or a change in SM level. Given that pharmaceutical product marketing regulatory agencies, such as the Spanish Pharmaceutical product Agency, the European Medicine Agency (EMA) and the Food and Drug Administration request the existence of monitoring methodologies for assessment of pharmaceutical product effectiveness, the identification of molecules whose changes in expression or activity (among others) might predict the efficiency of a compound, is advisable in order to guarantee patients to receive proper medical assistance. Thus, related inventions can be considered all those that allow an accurate application of the treatments. The present invention refers to the synthesis of a series of 2-hydroxide fatty acids derivatives, the separation of their racemic forms and their therapeutic uses. Furthermore, the present invention also comprises the description of target cells, its activity and, moreover description of biomarkers which allow to determine the effectiveness of said compounds, as well as process used for that purposes.

Moreover, it is important to find compounds which can regulate the activity of other enzymes involved in lipid metabolism, for example, the serine-palmitoil transferase enzyme (EC 2.3.1.50); or the estearoil-CoA desaturase enzyme (ECD, EC 1.14.19.1) which is responsible for the synthesis of oleic acid. The ceramide produced by the activity of EC 2.3.1.50 is a lipid molecule of great biological interest. An important role of the ceramide is that it takes part in the induction of apoptosis, also known as programmed cell death (Lladó et al., 2010). Apoptosis is a highly regulated biological process whose function is to eliminate useless cells or cells that are a threat to the health of the organism. In this way, tumoral cells often develop molecular mechanisms to escape apoptosis (Lladó et al., 2010).

DESCRIPTION OF THE INVENTION

Brief Description

Preferably, this invention focuses on resolving the changes in levels of SM in cells, so as to find compounds which can reverse the levels of change of enzyme EC 2.7.8.27 by activation (if the enzyme is infra-expressed or has a reduced activity) or by inhibition (if the enzyme is over-expressed or has an increased activity), thus controlling levels of SM synthesised by the enzyme and so reversing pathological processes caused by deregulation of the enzyme or by abnormal levels of SM.

To achieve this end this invention carried out a procedure of synthesis and isolation of enantiomers [−] and [+] of compound 2-hydroxidederivates in fatty acids which, as will be seen later on in the examples, are able to regulate the activity of enzyme EC 2.7.8.27 and so the level of synthesised SM. These fatty acids show a longer half-life in the blood than natural fatty acids. In fact, this invention refers to pharmaceutical compounds which include the aforesaid enantiomers, and to their use as medicaments for treating diseases whose shared etiology is based on changes (of whatever origin) in the lipids of the cell membrane like, for example: changes in the level, composition, or structure of these lipids, and also in the treatment of diseases where regulating the lipid structure and composition of the membrane can induce a reversion to the pathological state. The therapeutic effect is achieved, preferably, by regulating (activating or inhibiting) the activity of enzyme EC 2.7.8.27 and/or the level of its product, SM or even the level of GFAP and/or DHFR.

Apart from the regulation of enzyme EC 2.7.8.27, this invention shows that compound 2OHOA regulates the activity of other enzymes involved in lipid metabolism, for example in U118 cells. Thus, we investigated enzyme EC 2.3.1.50. In this invention we show how 2OHOA stimulates the activity of EC 2.3.1.50 (example 8 and FIG. 9), provoking the programmed death of cells in human leukaemia cells. On the other hand, an important reduction in the levels of oleic acid was detected in the membranes of U118 cells treated with 2OHOA, showing that 2OHOA is an important inhibitor of enzyme EC 1.14.19.1, the enzyme responsible for the synthesis of oleic acid from estearic acid (Example 9 and FIG. 10). At this respect it is important to point out that both EC 2.7.8.27 and EC 2.3.1.50 are enzymes corresponding to sphingolipid metabolism, which are interrelated by belonging to the metabolic pathway of the same type of molecules. On the other hand, EC 1.14.19.1 enzyme is a fatty acid modifier. Its relation with the other two enzymes is that sphingolipid always have fatty acid chains in their structure. As each fatty acid provides different properties to sphingolipids, the fact that they can be modified have effect in their biological activity. Thus, it is possible to state that the three enzymes mentioned herein are closely interrelated and therefore is normal that just one molecule can regulate the activity of the three enzymes.

The enantiomers [−] (also isomer S) and [+] (also isomer R) in this invention are distinguished by the direction of deviation of polarised light. If the optic isomer deviates polarised light to the right (clockwise), it is represented with the sign [+] (this is the dextrogyrous isomer or dexter form). However, if the optic isomer deviates polarised light to the left (anticlockwise), it is represented as [−] (this is the levogyrous isomer or levo form).

Specifically then, this invention shows that the [−] enantiomer of compound 2-hydroxidederivates in fatty acids acts as an activator for said enzyme, positively regulating synthesis of SM, a sphingolipid which, as explained above, is the main presence in the membranes of human and animal cells and is essential for the correct structure of the double lipid layer and the functioning of the cell. Thus, [−] enantiomer can be used to prepare a pharmaceutical compound for the treatment of pathologies which share a common aetiology where there are structural and/or function changes to the lipids in the cell membrane such as: cancer, obesity, hypertension, diabetes, etc, caused by an abnormally low activity of the abovementioned enzyme EC 2.7.8.27. Furthermore, the racemic form is an activator of this enzyme, since the activity of isomer [−] (which is the active one) over isomer [+] (which does not induce enzyme activity), is predominant. At this respect, the positive activity of the racemic form is believed to be caused by the fact that an activation which induces the synthesis of new SM molecules is more important than the inhibition which can silence enzyme molecules which were not previously actives. In any case, the activation potency of the racemic form is lower than the one of the enantiomer [−], which explains the lower therapeutic activity of the aforesaid racemic form.

As can be seen from the examples in this invention, it is important to note that enantiomer [−] of compound 2-hydroxidederivates in fatty acids shows an improved therapeutic effect compared to the racemic (which contains equal quantities of both enantiomers). What is more, we should emphasise that enantiomer [−] of compound 2-hydroxidederivates in fatty acids has lower toxicity and fewer side effects than enantiomer [+] (see Table 3, Example 7).

Furthermore, this invention also shows that enantiomer [+] of compound 2-hydroxidederivates in fatty acids acts as an inhibitor for enzyme EC 2.7.8.27, negatively regulating the synthesis of SM, and may be used in basic research for studies of the regulation of enzyme EC 2.7.8.27, or for treating diseases characterised by an abnormally high activity of enzyme EC 2.7.8.27, and/or an abnormally high level of SM such as, for example, cystic fibrosis (Slomiany et al., 1982). On the other hand, high levels of cholesterol are associated with important cardiovascular alterations. At this respect, cholesterol usually associates with SM in order to form very ordered membrane domains, known in scientific literature as "lipid rafts" or "Lo" (i.e. liquid ordered). The cholesterol increase favours the increase of these lipid regions, which result in changes in the cellular signalization which can lead to apparition of different cardiovascular and metabolic diseases or alterations. Thus, SM level reduction in hypercholesterolemia and hypertriglyceridemia can help to reduce cholesterol and triglyceride levels in plasma and membranes. Accordingly, enantiomer [+] would play a protective role in several types of disorders, such as hypercholesterolemia and hypertriglyceridemia, since it induces a reduction in the seric levels of said lipids, as well as reductions in the SM levels which lead to lipid rafts density reduction in cells.

In addition, given that enzyme EC 2.7.8.27 is responsible for the synthesis of SM and, therefore, for the correct structure and functioning of the cell membrane, we can consider both the enzyme and the SM as molecular markers to be used to carry out a method for the in vitro diagnosis and/or prognosis of diseases based on changes in the cell membrane. Said changes are not naturally occurring, they are caused by the activity of compounds herein described, instead. Furthermore, we have been able to confirm that compounds of the present invention also regulate levels of GFAP and/or DHFR proteins. As a result, this invention also refers to a method/kit for carrying out diagnosis or prognosis of such pathologies, which comprises reagents or means which can evaluate the activity of enzyme EC 2.7.8.27 and/or the level of SM, GFAP or DHFR thus implementing the diagnosis/prognosis as a method for monitoring the efficiency of the patient's treatment.

For this reason, said enzyme and/or its product, SM, can be seen as therapeutic targets at which to direct molecules capable of regulating the activity of the enzyme and/or the level of SM, and so reverse pathological processes that have developed or are about to develop in the future as a result of the changes in the activity of the enzyme or the level of SM, GFAP or DHFR. As an example, enantiomer [−] in the invention illustrates the possible use of enzyme EC 2.7.8.27 as a therapeutic target, when activating its enzymatic function in pathological processes where this function is in deficit so as to re-establish normal levels of SM. On the other hand, measuring the activity of enzyme EC 2.7.8.27 and/or the level of SM, and/or the level of GFAP and/or the level of DHFR are also useful for carrying out screening processes for possible compounds to obtain other molecules which, like enantiomers [−] and [+] in the invention, are able to regulate the activity of enzyme EC 2.7.8.27 and/or the level of SM, and/or the level of GFAP and/or the level of DHFR, thus reversing pathological processes.

In consequence, this invention shows the particular importance of selecting compounds with exclusive structural characteristics like: fatty acids with at least one double bond, with a total number of carbon (C) atoms equal to or less than 20, and a radical substitute, especially the hydroxyle radical (OH) in carbon 2 (or carbon α).

To be precise, this invention refers to compounds that are enantiomers [−] and [+] of Formula I:

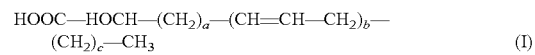

where a, b and c take independent values between 0 and 6, bearing in mind that the total number of carbons in the molecule is ≤20.

Furthermore, we establish that the preferred therapeutic form of the invention is enantiomers [−] (corresponding to form S) of Formula I, which is shown to be the most effective form for activating enzyme EC 2.7.8.27, more than the racemic form, and enantiomer [+] (corresponding to form R) of Formula I which is seen to be an inhibitor of enzyme EC 2.7.8.27.

As a preferred embodiment, this invention particularly refers to enantiomers [−] and [+] of Formula I with the following values for a, b and c:

TABLE 1

| Formula | a | b | c |
|---|---|---|---|
| HOOC—HOCH—$(CH_2)_6$—$(CH=CH—CH_2)_1$—$(CH_2)_4$—$CH_3$ | 6 | 1 | 4 |
| HOOC—HOCH—$(CH_2)_6$—$(CH=CH—CH_2)_1$—$(CH_2)_6$—$CH_3$ | 6 | 1 | 6 |
| HOOC—HOCH—$(CH_2)_6$—$(CH=CH—CH_2)_2$—$(CH_2)_3$—$CH_3$ | 6 | 2 | 3 |
| HOOC—HOCH—$(CH_2)_6$—$(CH=CH—CH_2)_3$—$(CH_2)_0$—$CH_3$ | 6 | 3 | 0 |
| HOOC—HOCH—$(CH_2)_3$—$(CH=CH—CH_2)_3$—$(CH_2)_3$—$CH_3$ | 3 | 3 | 3 |

As a preferred embodiment, this invention particularly refers to enantiomer [−] of Formula I[−] HOOC—HOCH—$(CH_2)_6$—$(CH=CH—CH_2)_1$—$(CH_2)_6$—$CH_3$, in this invention named as [−]2OHOA.

Another preferred embodiment in this invention is the reference to enantiomer [+] of Formula I [+]HOOC—HOCH—$(CH_2)_6$—$(CH=CH—CH_2)_1$—$(CH_2)_6$—$CH_3$, in this invention named as [+]2OHOA.

As a way of example, diseases characterised by a deficit in the activity of enzyme EC 2.7.8.27 and so by an abnormally low level of SM in the cell membrane and which could be treated with enantiomer [−] of this invention include:

Cancer: prostate cancer, breast cancer, cancer of the pancreas, leukaemia, cancer of the uterus, cancer of the colon, brain cancer, lung cancer (see Table 2).

Vascular pathologies: hypertension, arteriosclerosis, cardiomyopathies, angiogenesis, cardiac hyperplasia, etc.

Metabolic pathologies: diabetes, metabolic syndrome or obesity.

Other pathologies: lesions to the medulla, Alzheimer's disease, sclerosis, cellulitis, etc.

So, more specifically, the first part of this invention refers to an enantiomer [−] or [+] a compound of Formula I:

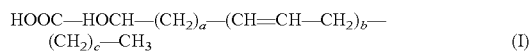

$$\text{HOOC—HOCH—}(CH_2)_a\text{—}(CH=CH—CH_2)_b\text{—}(CH_2)_c\text{—}CH_3 \quad (I)$$

characterised because a, b and c take independent values between 0 and 6, bearing in mind that the total number of carbons in the molecule is ≤20. Preferably for the invention, the compound is the result of the selection of at least one of the following combinations of values for a, b and c: a=6, b=1 y c=6; a=6, b=1 y c=4; a=6, b=2 y c=3; a=6, b=3 y c=0; y a=3, b=3 y c=3.

Another preferred embodiment of this invention refers to compounds with the formula: [+]HOOC—HOCH—$(CH_2)_6$—$(CH=CH—CH_2)_1$—$(CH_2)_6$—$CH_3$. As way of example, diseases characterised by an excess of enzyme EC 2.7.8.27 activity, and consequently, by abnormally high level of SM in cellular membranes, and which could be treated or prevented with enantiomer [+] of the invention are cystic fibrosis, hypercholesterolemia and hypertriglyceridemia.

Another preferred embodiment of this invention refers to compounds with the formula: [−]HOOC—HOCH—$(CH_2)_6$—$(CH=CH—CH_2)_1$—$(CH_2)_6$—$CH_3$.

A second aspect of this invention refers to the use of at least one of the previously mentioned compounds for the preparation of a pharmaceutical composition for the treatment and/or prevention of pathologies whose common etiology shows structural and/or function changes in the cell membrane due to deregulation of the activity of enzyme EC 2.7.8.27 and/or in the concentration level of SM, the level of GFAP and/or the level of DHFR, in cells in general and in membranes in particular.

Moreover, the present invention covers at least one of the abovementioned compounds for use in the treatment and/or prevention of pathologies whose common etiology shows structural and/or functional alterations of the cell membrane, due to deregulation of enzyme EC 2.7.8.27 activity, the level or concentration of SM, the level of GFAP or the level of DHFR, generally in cells and particularly in membranes.

This invention even refers to the pharmaceutical composition itself, which comprises at least one of the aforementioned compound and, as an option, pharmaceutically acceptable vehicles. Thus, the compounds in this invention may be administered independently or formulated in pharmaceutical compositions which combine excipients such as: binding agents, fillers, disintegrators, lubricants, coverings, sweeteners, flavourings, colouring agents, transporters, etc, and combinations of these. At the same time, the compounds in this invention can form part of pharmaceutical combinations which combine other active ingredients.

To use the compounds in this invention as medicines, administration may be in any form, for example: by way of mouth (pills, capsules or syrups), by way of the digestive system, by way of the rectum (enemas, or suppositories), externally (creams and plasters), by inhaler, by parenteral injection, by intravenous injection, by intramuscular injection, or by subcutaneous injection, as indicated above or in any other acceptable pharmaceutical form like: methyls, ethyls, phosphates, or other radicals like ester, ether, alquile, etc.

As a preferred embodiment, this invention refers to the use of compound [−]HOOC—HOCH—(CH2)$_6$-(CH=CH—CH2)$_1$-(CH2)$_6$-$CH_3$ for the preparation of a pharmaceutical composition for the treatment and/or prevention of pathologies whose common etiology shows structural and/or function changes in the cell membrane due to a deficit in the activity of enzyme EC 2.7.8.27 and/or to an abnormally low level of SM in the cell membrane, an abnormally low level of GFAP or an abnormally high level of DHFR; preferably choosing pathologies among: prostate cancer, breast cancer, cancer of the pancreas, leukaemia, cancer of the uterus, cancer of the colon, brain cancer, lung cancer, malignant melanoma and liver cancer; Vascular pathologies: hypertension, arteriosclerosis, cardiomyopathies, angiogenesis, cardiac hyperplasia; Metabolic pathologies: hypercholesterolemia, hypertriglyceridemia, diabetes, metabolic syndrome or obesity.

Additionally, the present invention refers to the use of a compound [−]HOOC—HOCH—(CH2)$_6$-(CH=CH—CH2)$_1$-(CH2)$_6$-$CH_3$ in the treatment and/or prevention of pathologies whose common etiology shows structural and functional alterations in the cell membrane, due to a deficit on the EC 2.7.8.27 enzyme activity, an abnormally low level of SM in the membrane cell, an abnormally low level of GFAP or an abnormally high level of DHFR, being the pathologies preferably selected among: cancer preferably prostate cancer, breast cancer, cancer of the pancreas, leukaemia, cancer of the uterus, cancer of the colon, brain cancer, lung cancer, malignant melanoma and liver cancer; vascular pathologies preferably hypertension, arteriosclerosis, cardiomyopathies, angiogenesis, cardiac hyperplasia, or metabolic pathologies preferably diabetes, metabolic syndrome or obesity.

In other preferred aspect, the invention refers to the use of a compound of formula [+]HOOC—HOCH—(CH2)$_6$-

(CH═CH—CH2)$_1$-(CH2)$_6$-CH$_3$ in the preparation of a pharmaceutical composition for the treatment and/or prevention of pathologies whose common etiology show functional and/or structural alterations in the cellular membrane due to an excessive activity of EC 2.7.8.27 enzyme, an abnormally high level of SM in the membrane cell, an abnormally high level of GFAP or an abnormally low level of DHFR being the pathology, for example, cystic fibrosis, hypercholesterolemia and hypertriglyceridemia.

Likewise, this invention refers to the use of the compound formula [+]HOOC—HOCH—(CH2)$_6$-(CH═CH—CH2)$_1$-(CH2)$_6$-CH$_3$ for the preparation of a pharmaceutical composition for the treatment and/or prevention of pathologies whose common etiology shows structural and/or function changes in the cell membrane due to excess activity of enzyme EC 2.7.8.27 and/or to an abnormally high level of SM, an abnormally high level of GFAP or an abnormally low level of DHFR in the cell membrane, for example, the pathology cystic fibrosis hypercholesterolemia and hypertriglyceridemia.

A third aspect of this invention refers to a method for treating and/or preventing pathologies whose common etiology shows structural and/or function changes in the cell membrane due to deregulation of the activity of enzyme EC 2.7.8.27 and/or in the concentration level of SM, the level of GFAP or the level of DHFR, which comprises administration to the patient of a therapeutically effective amount of at least one of the previously mentioned compounds or compositions which include them.

As a preferred embodiment, this invention refers to a method for treating and/or preventing pathologies whose common etiology shows structural and/or function changes in the cell membrane due to a deficit in the activity of enzyme EC 2.7.8.27 and/or an abnormally low level of SM in the cell membrane, and comprises administration to the patient of a therapeutically effective amount of compound [−]HOOC—HOCH—(CH2)$_6$-(CH═CH—CH2)$_1$-(CH2)$_6$-CH$_3$ or a composition that contains it. In a preferred embodiment, pathologies are preferably chosen among: cancer preferably prostate cancer, breast cancer, cancer of the pancreas, leukaemia, cancer of the uterus, cancer of the colon, brain cancer, lung cancer; Vascular pathologies: hypertension, arteriosclerosis, cardiomyopathies, angiogenesis, cardiac hyperplasia; Metabolic pathologies: hypercholesterolemia, hypertriglyceridemia, diabetes, metabolic syndrome or obesity.

Another preferred embodiment of this invention refers to a method for treating and/or preventing pathologies whose common etiology shows structural and/or function changes in the cell membrane due to excess activity of enzyme EC 2.7.8.27 and/or an abnormally high level of SM in the cell membrane, and comprises administration to the patient of a therapeutically effective amount of compound [+]HOOC—HOCH—(CH2)$_6$-(CH═CH—CH2)$_1$-(CH2)$_6$-CH$_3$ or a composition that contains it. A preference, for example, is the pathology cystic fibrosis, hypercholesterolemia and hypertriglyceridemia.

To all effects of this invention "a therapeutically effective amount" means an amount which reverses the disease or prevents it with no adverse side effects. "A therapeutically effective amount" is also that which has a significant therapeutic effect with an acceptable level of toxicity where the disease being treated is very serious or lethal.

A fourth part of this invention refers to an in vitro method for choosing possible compounds which are useful for treating and/or preventing pathologies whose common etiology shows structural and/or function changes in the cell membrane and comprises an evaluation of the activity of enzyme EC 2.7.8.27, of the level of SM, of the level of GFAP or of the level of DHFR in the presence of a possible compound. i.e, this invention comprises the use of enzyme EC 2.7.8.27, or of the SM, GFAP or DHFR themselves, as therapeutic targets at which to direct compounds so as to treat and/or prevent the pathologies described above, with the aim of designing therapeutic tools capable of altering the activities or levels thereof (for example FIG. 5) and to which addressing compounds with the purpose of preventing and/or treating the abovementioned pathologies.

A fifth part of this invention refers to an in vitro method for prognosis/diagnosis of pathologies whose common etiology shows structural and/or function changes in lipids in the cell membrane and comprises determining the deregulation of the activity of enzyme EC 2.7.8.27, and/or the presence of abnormal levels of SM, of GFAP or of DHFR in the cell membranes or other parts of the cell. This invention, then, comprises the use of enzyme EC 2.7.8.27, or of the SM, GFAP or DHFR themselves, as a molecular marker to enable prognosis/diagnosis of the pathologies described above. The importance of SM in the structure and activity of the cell membrane, and of in the cell membrane and comprises determining the deregulation of the activity of enzyme EC 2.7.8.27 for the production of this phospholipid, make detection of the cellular concentration/activity of both in tissues, plasma, cephaloraquidic liquid, urine and/or other body fluids a tool for creating kits for detecting, diagnosing and monitoring of the different pathologies contemplated in this invention, such as: cancer, hypertension, obesity and metabolic diseases. For this reason, both SM and enzyme EC 2.7.8.27 are bio-markers for detecting human diseases and, as we saw above, are therapeutic targets for designing new therapies for humans.

A preferred embodiment of this invention refers to an in vitro method for prognosis/diagnosis of pathologies whose common etiology shows structural and/or function changes in lipids in the cell membrane and comprises determining the deficit in the activity of enzyme EC 2.7.8.27 and/or of abnormally low levels of SM, and/or of abnormally low levels of GFAP or of abnormally high levels of DHFR in the cell membrane, preferably choosing pathologies among: cancer preferably prostate cancer, breast cancer, cancer of the pancreas, leukaemia, cancer of the uterus, cancer of the colon, brain cancer, lung cancer, malignant melanoma and liver cancer; Vascular pathologies preferably hypertension, arteriosclerosis, cardiomyopathies, ictus, angiogenesis, cardiac hyperplasia; Metabolic pathologies: hypercholesterolemia, hypertriglyceridemia, diabetes, metabolic syndrome or obesity.

Another preferred embodiment of this invention refers to an in vitro method for the prognosis/diagnosis of pathologies whose common etiology shows structural and/or function changes to lipids in the cell membrane due to excess activity of enzyme EC 2.7.8.27 and/or an abnormally high level of SM in the cell membrane, where the preference, for example, is the pathology cystic fibrosis hypercholesterolemia and hypertriglyceridemia.

The sixth part of this invention refers to kits for use as a method for prognosis/diagnosis as described above comprising useful means for determining the activity of enzyme EC 2.7.8.27 and/or the level of SM, and/or the level of GFAP and/or the level of DHFR in the cell membrane. These useful means comprise TLC and HPTLC techniques, gas chromatography, image analysis, absorption spectroscopy or fluorescence, optic microscopy, fluorescence and confocal microscopy, immunoblotting, immunocytochemistry, ELISA or similar techniques (RIA, dot/slot blot, EIA, etc.).

In a preferred embodiment, the kit is characterized in that the prognosis/diagnosis is performed though direct sphingomyelin level quantification, and/or its indirect quantification by means of its precursors (for example, phosphatdyethanolamine, phosphatidylcholine, ceramide, etc.) or its derivatives (for example sphingolipids). Preferably, the precursor is ceramide, NBD-Cer derivative or NBD-SM and the indirect measurement is made by means of lysenin.

Another aspect of this invention refers to method for isolating and purifying the 2OHOA enantiomers which involves the following steps:

1. Hydroxylation in acid medium of the unsaturated fatty acid for producing the racemic product.
2. Purification by recrystallization and precipitation of the racemic fatty 2-hydroxiolate in its sodium salt form.
3. Sterilisation of the racemic mixture of 2-hydroxiolate sodium with a solution of sulphuric acid in ethanol, preferably at 10%.
4. Enantio-selective hydrolysis of the ester, catalysed by the lipase *pseudomonas fluorescens* (Amane Lipase, cas #9001-62-1) at 25° C.
5. Control of the progress of the reaction using liquid chromatography.
6. Hydrolysis of the mixture with diluted HCl to a pH less than 2.
7. Extraction of products in methyl-perbutile-ether (MTBE) and organic phase cleaning.
8. Elimination of solvent in a vacuum so as to obtain a raw material with the mixture of acid and ester.
9. Separation of acid and ester by crystalising the former.
10. Return to step 1 in the acid phase and step 2 for the ester to start the reprocessing of each isolated fraction (acid and ester) until the desired enantiometric purity is achieved. (95% of enantiometric excess, which equates to 97.5% of desired enantiomer and 2.5% of the unwanted enantiomer).

Separation and isolation of the two 2OHOA enantiomers is not known to date. Due to the technical difficulty of isolating [−] enantiomer, this has not been carried out to date.

The present invention also refers to an in vitro method for monitoring cell alterations produced on sick cells by effect of the compounds of present invention, or other compounds, which act on the same cell process or on related cell processes, producing the cure or improvement of patient's affected cells. That is to say, the present invention comprises the use of EC 2.7.8.27 enzyme or SM, GFAP or DHFR as molecular markers, whose changes induced by the treatment with the molecules of the present invention, make possible to know if the patient is reacting to treatment and, therefore, determine its effectiveness and the period of time it should be maintained. These methods can also make possible to predict if a patient has possibilities of reacting to treatment with the molecules of the present invention, thus they can be used for making the diagnosis and/or prognosis of the abovementioned pathologies. Given that membrane composition alteration and, precisely of SM levels, induces changes in the levels of GFAP and DHFR proteins, a preferred aspect of the present invention refers to a method that makes possible to follow the changes induced by the molecules of the present invention or other molecules which have a similar effect on the pathological cells. Therefore, the use of SM, EC 2.7.8.27 enzyme, GFAP and/or DHFR gives the possibility of making the applied therapy to change its levels or activity. The purpose of this determination is (1) the prediction of the effectiveness of the treatment in order to prevent potentially non-reactive patients from following an ineffective therapy and (2) knowing the patient's evolution in order to confirm that he or she reacts to therapy and know which doses to deliver depending on the treatment stage, as well as the duration of said stages and of the treatment itself as a whole. Since these aspects are critical for avoiding unnecessary pharmaceutical expenditure and for being able to apply the most rational therapy possible, big pharmaceutical regulatory agencies request the existence of biomarkers and diagnosis systems as the ones described herein.

Similarly, the present invention refers to a method for treating patients suffering from the abovementioned pathologies, which comprises the determination, of the presence of said deregulation of EC 2.7.8.27 enzyme, of the level of SM, of the level of GFAP or of the level of DHFR, themselves, and of the treatment of patient which presents said deregulation with the compounds of the invention.

In addition, the present invention refers to a method for selecting the therapy for a patient with a pathology described in the present invention which comprises the determination of the existence of said deregulation in EC 2.7.8.27 enzyme, of the level of SM, of the level of GFAP or of the level of DHFR and the selection based on said determination, of a therapy based in the compounds of the present invention.

The following definitions are included with the purpose of illustrating the present invention:

High/low activity of EC 2.7.8.27 enzyme: enzymatic activity which results in the appearance of high or low levels, respectively, of SM in membranes.

High/low level of sphingomyelin: it is considered that low levels of sphingomyelin are those below the 15% of the total phospholipids in the membrane. It is considered that high levels of sphingomyelin are those above the 15% of this phospholipid, with respect to the total phospholipids.

High/low level of GFAP: it is considered that a high level of GFAP is the one that doubles or is even above ($\geq 200\%$) the normal levels present at the glia cells, with reference to the total milligrams of protein. It is considered that a low level of GFAP is the one that implies levels of half or even below ($\leq 50\%$) the normal levels present at the glia cells, with reference to the total milligrams of protein.

High/low level of DHFR: it is considered that a high level of DHFR is the one that doubles or is even above ($\geq 200\%$) the normal levels present at the quiescent cells whatever type they may be, with reference to the total milligrams of protein. It is considered that a low level of GFAP is the one that implies levels of half or even below ($\leq 50\%$) the normal levels present at the quiescent cells whatever type they may be, with reference to the total milligrams of protein.

A BRIEF DESCRIPTION OF THE FIGURES

FIG. 1

A. Compound 2OHOA induces a significant increase in the synthesis of SM in different cellular lines in human cerebral cancer (U118, SF767 and 1321N1), cells in human lung cancer (A549) and cells in human leukaemia (Jurkat), but not in non-tumoral cells (fibroblast cells in the human lung MRC5). At the same time, we have studied the anti-tumoral effect on these and other tumoral lines (see Table 2). The cells were treated in vehicle (water with 5% ethanol, control) or with compound 2OHOA for 24 hours in a concentration of 200 µM. The values of the ordinate axis represent the average±ESM (error standard mean for a number of experiments n=3-5) of SM levels (percent of total phospholipids), determined by chromatographic processes (followed by spectroscopy and image analysis), as a percentage of the total number of lipids compared with untreated cells (control). The levels of SM in tumoral cells are significantly lower than those in normal cells and compound 2OHOA only induced significant changes in cancer cells. These results show that enzyme EC 2.7.8.27 is a therapeutic target for the treatment of cancer and a bio-marker for monitoring the pathology and its evolution over several stages, and also that compound 2OHOA activates this enzyme and reverses the low levels of SM in cancer cells. In addition to the techniques for measuring enzyme activity and levels of SM described above, other techniques have been tested which lead to very similar results as, gas chromatography, confocal microscopy, fluorescence spectroscopy, etc.

B. Images of confocal microscopy showing marking of the cellular SM by means of a union of lysenin in human glioma cells U118 treated with a vehicle (Control) or with 2OHOA (200 μM). in the tumoral cells we can appreciate that the amount of membrane is scarce and that treatments with 2OHOA induce a dramatic increase in the quantity of SM in the membrane, a clear indicator that enzyme EC 2.7.8.27 has been activated. Furthermore, this experiment clearly shows that the increase in cellular SM level is mainly due to an accumulation in the plasmatic membrane of tumoral cells.

C. Upper panel: specific marking by immunocytochemical techniques of the SM (left: lysenin followed by an antibody marked with Alexa 488 fluorophore), of nuclear DNA with Hoechst 33258 (center: Hoechst) or both (right, merge). Figures correspond to human lung tumour sections (A549 cells) formed in immuno-depressed mice treated with a vehicle (control) or with [–]2OHOA at 600 mg/kg per day or at 900 mg/kg per day (oral administration, 50 days). These results clearly show how levels of SM significantly increase after treatment with [–]2OHOA, but do not increase naturally in said tumours.

Central panels: Detail of the marking of the SM (left), nuclear DNA (center) or both (right) in a cell present in a slice of a tumour developed in a human lung cancer-infected mouse (A549) and treated with [–]2OHOA (600 mg/kg per day, 50 days). Image shows nuclear DNA loss, clear indicator of the start of cellular death, in parallel with an increase of SM.

Bottom panel: The ordinate axis represents the quantification of the fluorescence intensity (arbitrary units) by confocal microscopy in slices of tumours shown in the upper panel (average+average standard deviation), coming from animals treated with a vehicle, or 2OHOA at 600 mg/kg per day (T600) or 900 mg/kg per day (T900) during 50 days. *** $P<0.001$.

D. A chart showing that the spectrophotometry determination of solution fluorescence of the SM levels is a very simple, quick and efficient analysis method.

Figure 2:
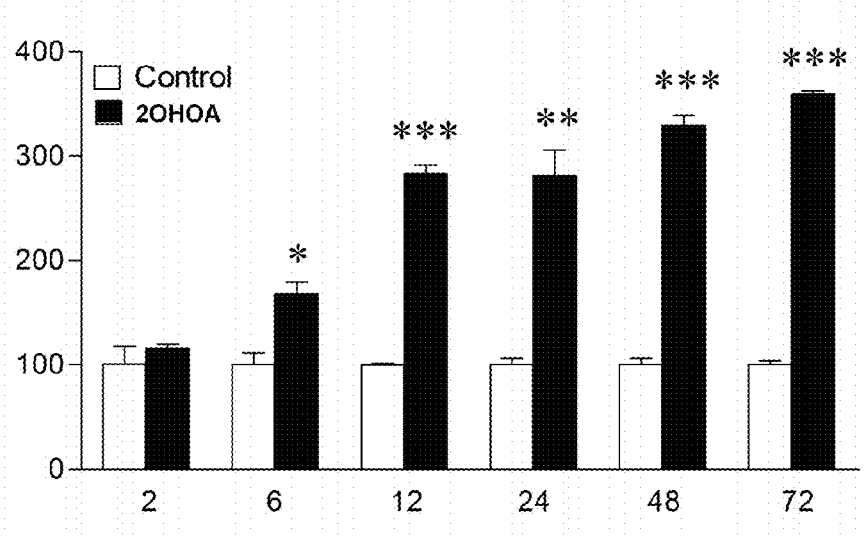
Figure 2:
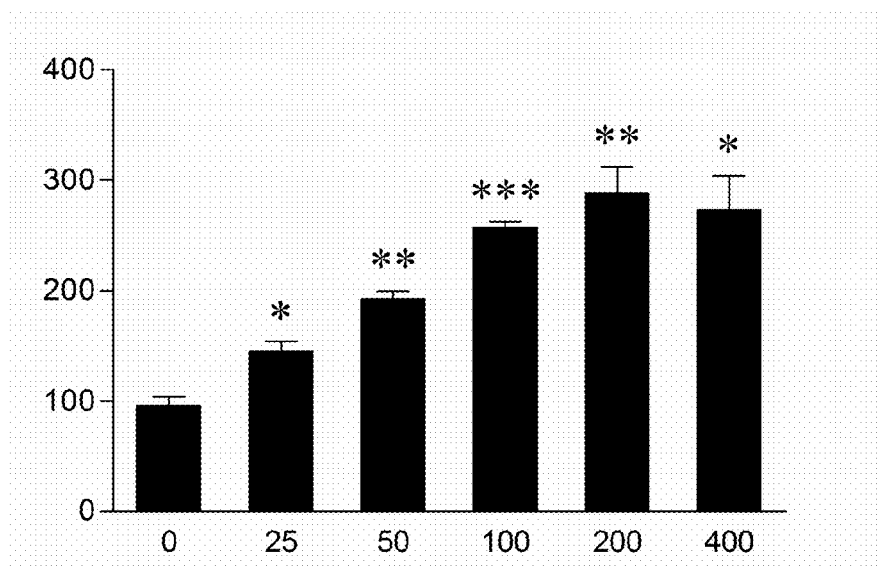

FIG. 2. Compound 2OHOA induces an increase in the synthesis of SM depending on concentration and the period of treatment. The values of the ordinate axis represent the average±ESM of levels of SM (percent of total phospholipids), compared to the untreated control (n=3-5). SM levels were determined by thinlayer chromatography (HP-TLC, high performance thin layer chromatography) and image analysis or gas chromatography:

A. Cancer cells of human glioma U118 treated at a 2OHOA concentration of 200 μM for different periods of time (2, 6, 12, 24, 48 y 72 hours). The white bars correspond to cells treated with a vehicle (control).

B. U118 cells treated for 24 hours at different 2OHOA concentrations (25-400 μM).

Figure 3:
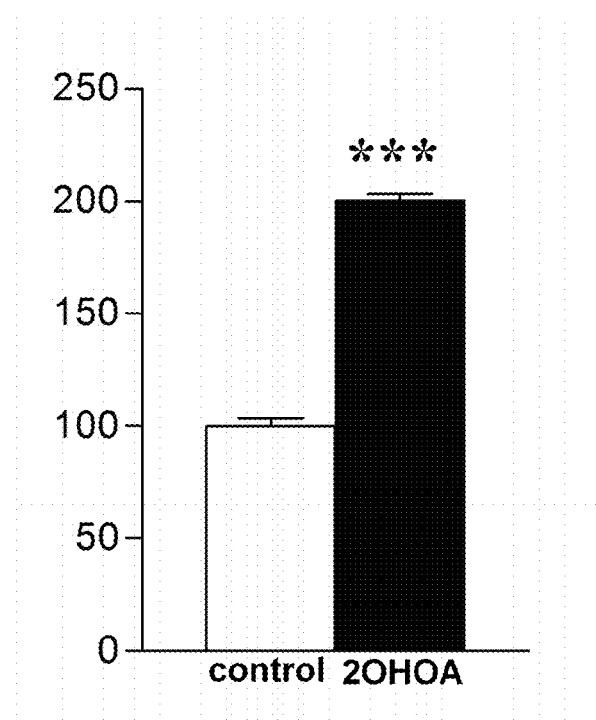

FIG. 3. Compound 2OHOA induces an increase in nuclear SM. U118 cancer cells were treated for 24 hours with a vehicle (control) or with 2OHOA at a concentration of 200 μM. The values of the ordinate axis represent the average±ESM (n=3-5) of levels of SM compared to the untreated control (100%).

Figure 4:
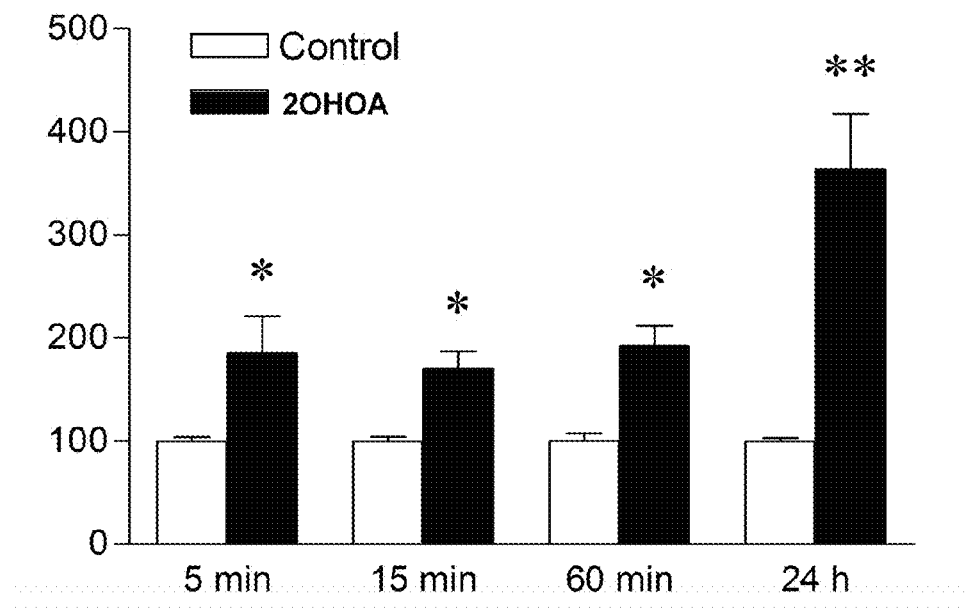
Figure 4:
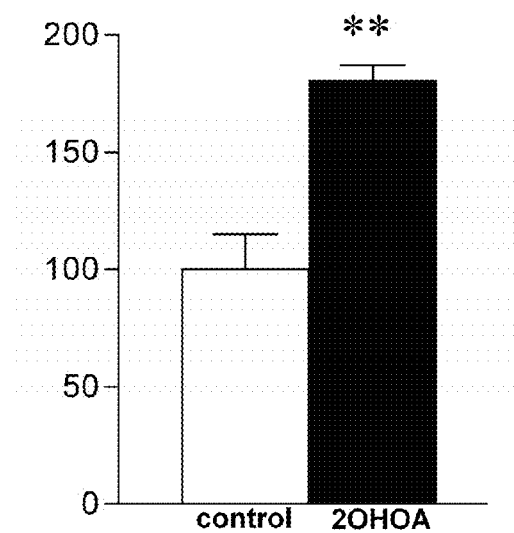
Figure 4:
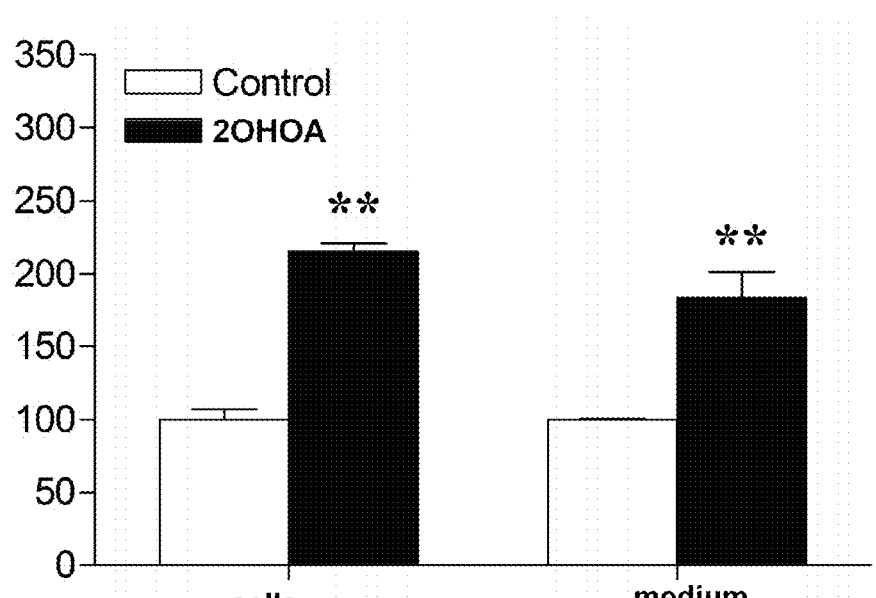

FIG. 4. Compound 2OHOA acts directly on enzyme EC 2.7.8.27. In A, B, C, in all cases, we incubated cells or cellular extracts or means of incubation with the fluorescent stratum of this enzyme NBD-Cer (nitro-benzoxadiazol-il) ceramide], in the presence or absence (control, white bars) of 2OHOA (black bars). Then, we extracted the lipids and determined the levels of formation of NBD-SM per HPTLC (HP-TLC, high performance thin layer chromatography). The values are presented on the ordinate axis as the average±ESM (n=3-5).

A. In vivo experiment of the activity of enzyme EC 2.7.8.27: we incubated U118 cells with NBD-Cer for 4 hours and then treated them with compound 2OHOA (200 μM) for different periods of time (5, 15, 60 minutes y 24 hours). Later, the cells homogenised and we measured the metabolisation of fluorofor NBD-Cer to become NBD-SM.

B. In vitro experiment of the activity of enzyme EC 2.7.8.27 in cellular extracts, where we measured the activity of the enzyme after killing the cells. This experiment shows that compound 2OHOA is able to activate enzyme EC 2.7.8.27 by direct interaction. For these experiments, homogenised cells were incubated with compound 2OHOA (200 μM) and NBD-Cer for 2 hours.

C. Effects of compound 2OHOA on the activity of isoforms 1 and 2 of enzyme EC 2.7.8.27. Activation of the isoforms EC 2.7.8.27 (1) and EC 2.7.8.27 (2) was determined by testing its activity on the cell surface.

Figure 5:
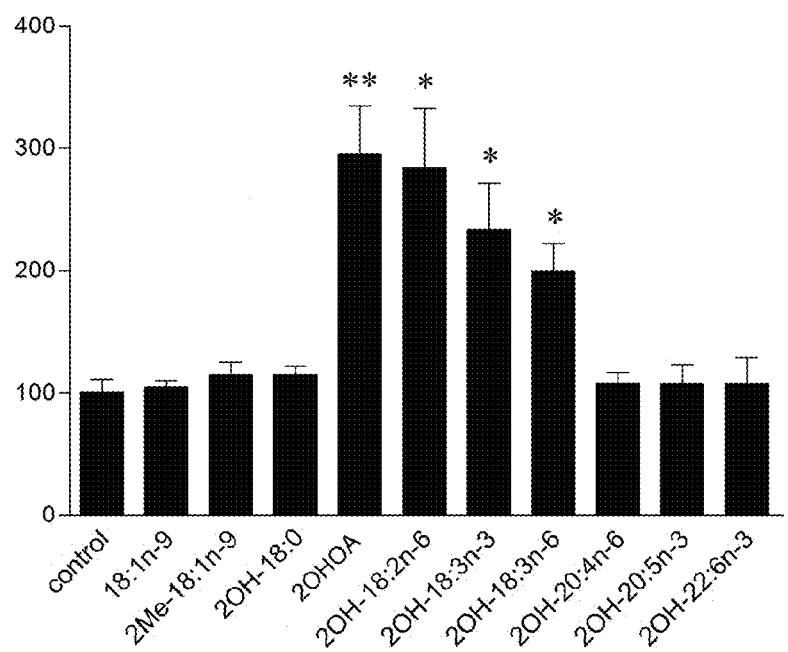

FIG. 5. The relation of structure-function in the activation of enzyme EC 2.7.8.27. Increase in SM in U118 cells induced by different fatty acids (200 μM, 24 h). Control: vehicle; 18:1n-9 (octadecenoic acid); 2Me-18:1n-9 (2-metiloctadecenoic acid); 2OH-16:1 (2-hydroxioctadecenoic acid); 2OH-18:0 (2-hydroxioctadecanoic acid); 2OHOA (2OH-18:1n-9, 2-hydroxioctadecenoic acid); 2OH-18:2n-6 (2-hydroxilinoleic acid); 2OH-18:3n-6 (2-hydroxi-γ-linolenic acid); 2M-18:3n-3 (2-hydroxi-α-linolenic acid); 2OH-20:4n-6 (2-hydroxiaraquidonic acid); 2OH-20:5n-3 (2-hydroxieicosapentaenoic acid); 2OH-22:6n-3 (2-hydroxidocosahexaenoic acid). The values of the ordinate axis represent the average±ESM (n=3-5) of levels of SM, determined by twin layer chromatography compared to the untreated control (100%). Fatty acids of 20 atoms of carbon or more produce no significant changes in the activity of this enzyme. The presence of other radicals in the carbon 2 (like H or $CH_3$) and the lack of double bonds in the fatty acid structure gave rise to inactive molecules.

FIG. 6.

A: This shows that changes in the cell membrane composition induce translocation of the Ras protein from the membrane to the cytoplasm. The high levels of 2OHOA and SM in the membrane impede the anchoring of the Ras protein on the membrane. The figure shows images of optic microscopy in phase contrast (Ph.C) of human glioma cells (SF767), and confocal microscopy, using a specific antibody against Ras which is marked fluorescently, after 10 minutes (confocal 1) and 24 hours (confocal 2) treated with a vehicle (control) or compound 2OHOA.

B: Translocation of the Ras protein impedes inactivation of the Raf protein and also the consequent activation of the signalling cascade of the MEK protein, as can be seen from the reduction in state of the (active) phosphorylased form of both proteins, determined by immunoblot in U118 cells cultivated in the absence (control) or non-presence of 150, 200 o 250 μM of 2OHOA.

C: Finally, there is a dramatic reduction in the state of activity of the protein MAP kinase (ERK1 y ERK2), also determined by immunoblot with specific anti-bodies at the concentrations of 2OHOA indicated in B.

D: The state of activity (levels of phosphorylased forms) of Akt and EGFR also decreases after incubating with 250 μM of 2OHOA.

In panels B to D the ordinate axis shows the percentage of phosphoprotein for untreated SF767 cells (control). The axis of abscises shows the (micromolar) concentration of compound 2OHOA.

E: Upper panel: Expression levels of DHFR in tumours derived from human glioma cells (SF767) implanted in hairless mice which were treated with 2OHOA during 50 days (600 mg/kg per day). Graph on the left shows fluorescence average values (n=4) determined by immunocytochemistry using a specific anti-body marked with fluorescence and photographs on the right correspond to a representative image. Bottom panel: Expression of DHFR in human lung cancer cells (A459). Each one of the experimental conditions and details of this graph is similar to the ones in the upper panel. These results demonstrates that levels of DHFR vary in response to treatment with molecules of the invention, so the activity or levels of this protein can be employed as biomarkers for monitoring the therapeutic efficiency of compounds described herein compounds acting in a similar way. Furthermore, it is deduced that tumours in which DHFR levels are high can respond well to the treatment with the compounds of present invention, so this protein is a good bio-marker for predicting the possible efficacy of the enantiomers of invention derived from fatty acids and, later on, show the effectiveness of the treatment with these compounds.

F: left panel: Levels of GFAP in serum of animals with human tumours (glioma) determined by immunoblotting. Hairless mice were infected with SF767 cells and treated with vehicle (glioma) or with 2OHOA (T, 600 mg/kg per day, 28 days). Immunoactivity against fragmented peptide from the GFAP (see photograph) in the serum of these animals, express as a percentage, was compared with the one found in animals without tumour and untreated (control). Right panel: the same, but determined by ELISA in serum of animals treated during 7 days (7d600) or 28 days (28d600) with 600 mg/kg of 2OHOA. An anti-body specifically against the GFAP was used in all experiments. These results demonstrates that levels of GFAP vary in response to treatment with molecules of the invention, so the activity or levels of this protein can be employed as biomarkers for following the therapeutic efficiency of compounds described herein o compounds acting in a similar way. Furthermore, it is deduced that tumours in which GFAP levels are low can react well to the treatment with the present invention compounds, so this protein is a good bio-marker for predicting the possible efficacy of enantiomers derived from fatty acids and, later on, show the effectiveness of the treatment with these compounds. Several techniques have been employed for the measurement of DHFR and GFAP, which include electrophoresis, immunoblotting, ELISA and similar techniques RT-PCR, etc. All these techniques and other similar ones can be employed in the determination of the levels and activity of DHFR and GFAP.

Figure 7:
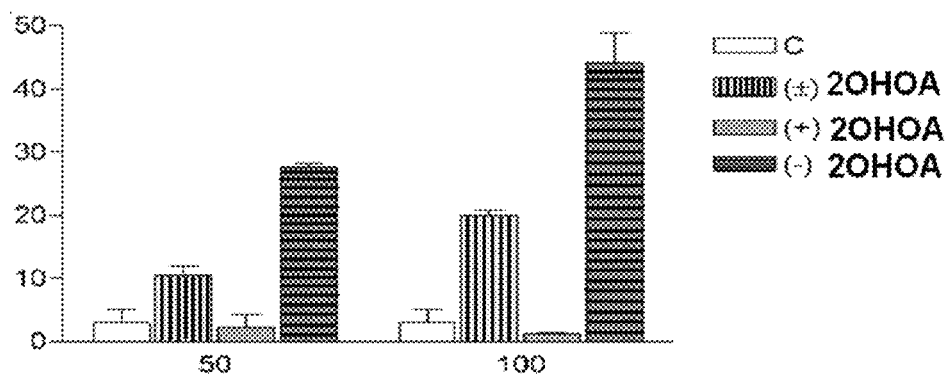
Figure 7:
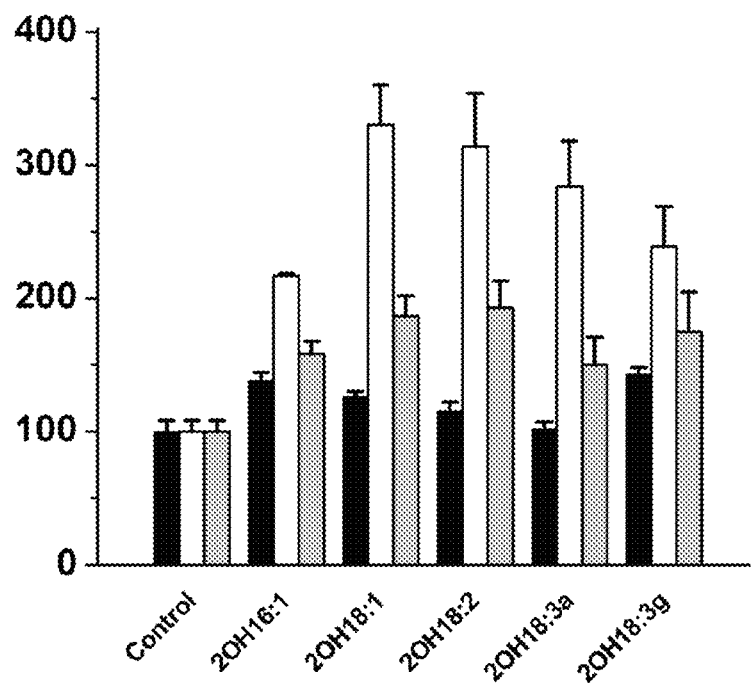

FIG. 7. A) Specificity of enantiomers [−] and [+], of the racemic mixture +/− of 2OHOA, in the activity of enzyme EC 2.7.8.27. The figure shows levels of SM (percentage SM of total lipids) in glioma U118 cells after treatment with the racemic mixture of 2-hydroxioleic acid (+/−), with compound [−]2OHOA and compound [+]2OHOA. The cells were treated for 24 hours at a concentration of 50 μM (50) and 100 μM (100). The ordinate axis values represent the average±ESM (n=3-5) of levels of SM determined by twin layer chromatography as a percentage of total lipids, compared with the levels in untreated cells (control). As we can see, enantiomer [−] produces an increase in SM, which indicates that it is an activator of enzyme EC 2.7.8.27, and enantiomer produces a reduction in levels of SM (especially obvious at a concentration of 100 μM [+]2OHOA), which indicates it is an inhibitor of the enzyme. In this context and without affecting at other levels, it is shown that mixtures containing this enantiomer induce the EC 2.7.8.27 enzyme activation, being the racemic a special case of molecular mixture, although a positive effect has been also seen in mixtures between enantiomer [−] and different vehicles or different therapeutic compounds. B) Effect of [+] forms (also enantiomer R: black columns), [−] (also enantiomer S: white columns) and racemic (grey columns) on the levels of SM in membranes of U118 cells (values measured after 24 h of incubation with 100 μM). Treatments employed were: vehicle (control), 2-hydroxypalmitoleic acid (2OH16:1), 2-hydroxyoleic acid (2OH18:1), 2-hydroxylinoleic acid (2OH18:2), 2-hydroxy-α-linoleic acid (2OH18:3a), and 2-hydroxy-γ-linoleic acid (2OH18:3g).

Figure 8:
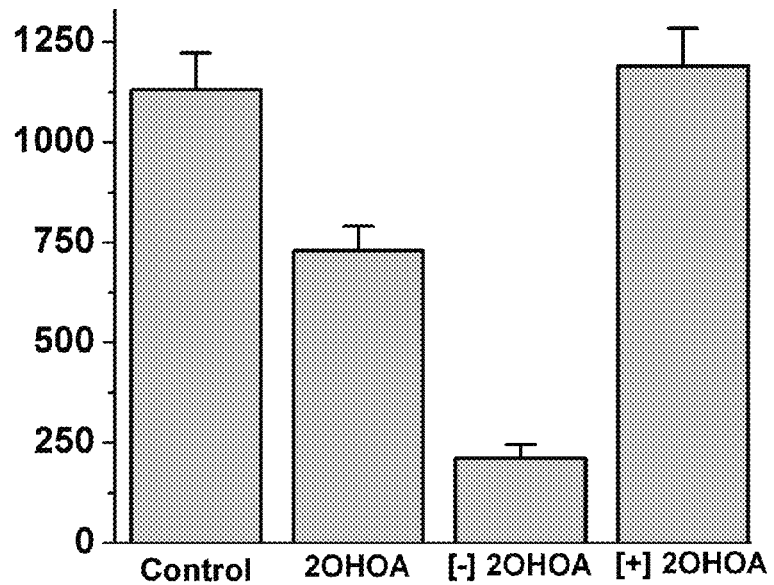
Figure 8:
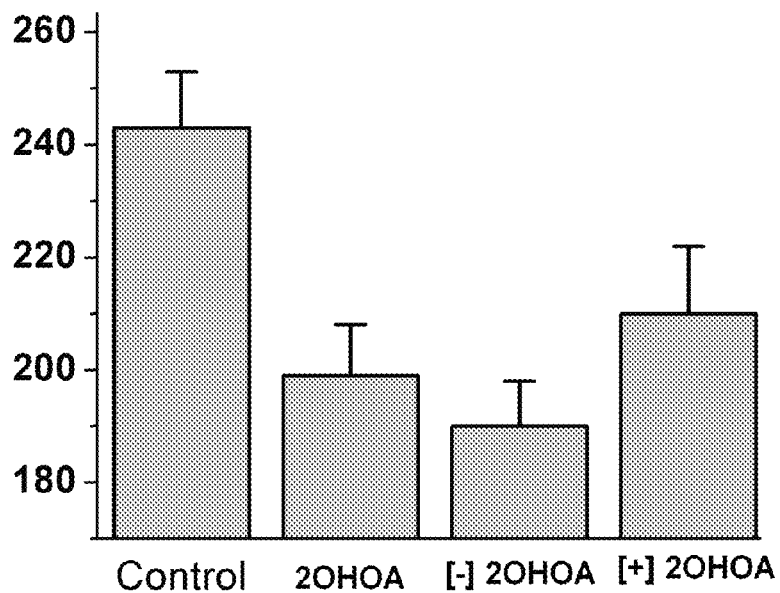
Figure 8:
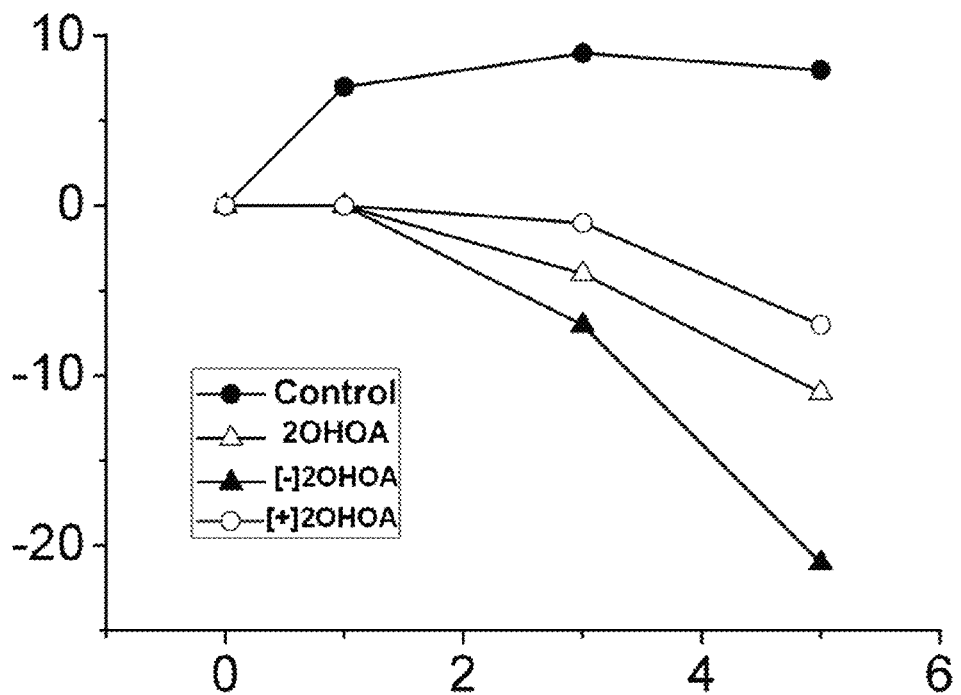
Figure 8:
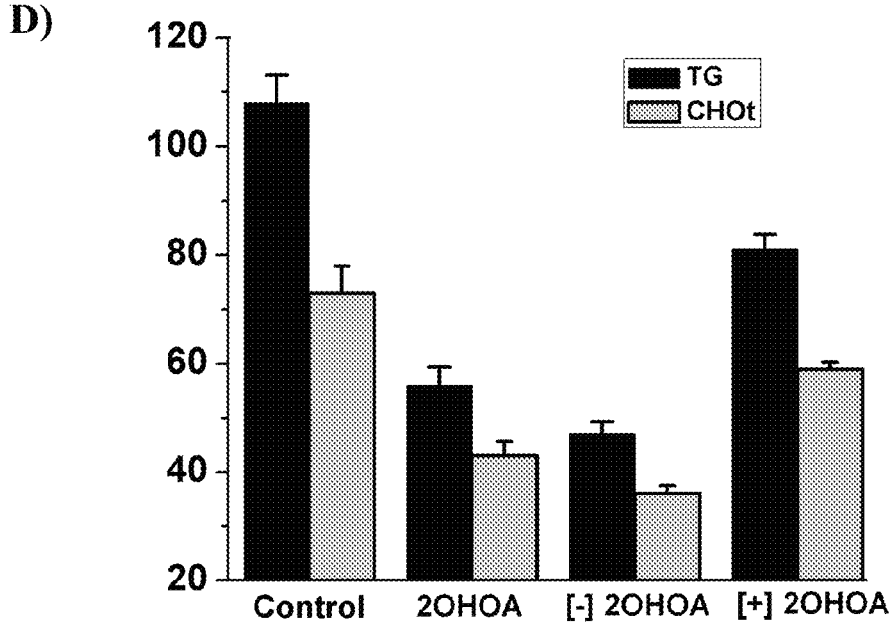
Figure 8:
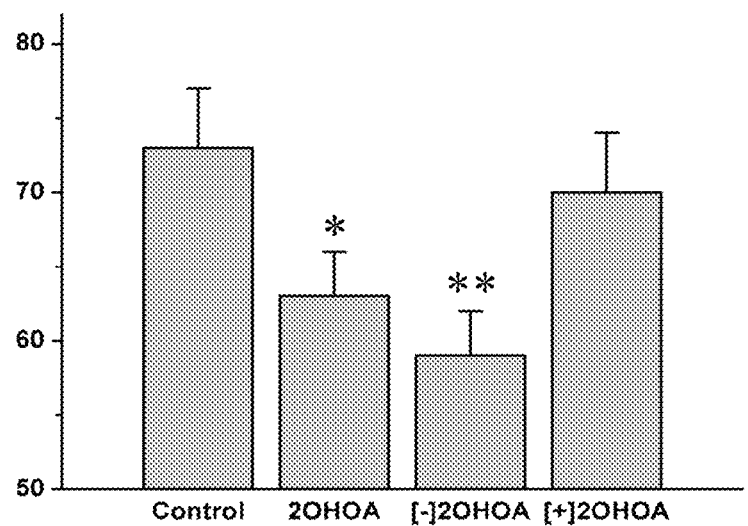

FIG. 8. This figure shows the effect of racemic (+/−) 2OHOA acid and optic isomers [−]2OHOA and [+]2OHOA on different pathological processes in animal models.

A. Effect on the volume of tumours derived from human lung cancer cells (A549): immuno-depressed mice were infected with human lung cancer cells and 7 days later (when the tumours were observable), treatments started with vehicle (control), 2OHOA racemic (+/−), and optic isomers [−]2OHOA and [+]2OHOA (600 mg/kg·day, 15 days, orally). The bars correspond to values of an average±EEM (n=3-5) of the increase in volume ($mm^3$) of the tumours (n=6). The treatment with 2OHOA racemic (+/−) induced significant reductions (P<0.01) compared with the control. Optic isomer [−]2OHOA induced significant reductions compared with all the other treatments (P<0.01).

B. Effects on arterial pressure: hypertense rats (strain SHR) were treated with 2OHOA racemic (+/−) and its optic isomers [−]2OHOA and [+]2OHOA (600 mg/kg every 12 h, 15 days, orally). All the molecules induced significant reductions (P<0.01) in systolic arterial pressure (mmHg, ordinate axis y) in SHR rats isomer [−]2OHOA being the most powerful in inducing hypotension effects. Values of average±EEM systolic pressure (n=6) are shown.

C. Effect on body weight: SHR rats were treated with 2OHOA racemic (+/−) and its optic isomers [−]2OHOA and [+]2OHOA (600 mg/kg·day, 5 days, orally). All the molecules induced significant reductions (P<0.01) in the animals' weight as from day 3 of treatment, isomer [−]2OHOA being the most powerful in inducing a reduction in body weight. Values of average±EEM body weight (abscises axis, n=6) are shown.

D. Effects on cholesterol and triglyceride levels: SHR rats were treated with 2OHOA racemic (+/−) and its optic isomers [−]2OHOA and [+]2OHOA (600 mg/kg every 12 h, 15 days, orally). All the molecules induced significant reductions (P<0.01) in the total triglyceride (TG) and cholesterol (CHOt) levels, optic isomer [−]2OHOA being the most powerful in inducing a reduction in the levels of these lipids. Values of average±EEM seric levels of lipids expressed as mg/dl (ordinate axis; n=6) are shown.

E. Effects on glycerine (plasmatic glucose levels): SHR rats were treated with vehicle (control), racemic 2OHOA and their optical isomers [−] 2OHOA and [+]2OHOA (600 mg/kg, 12 h, 15 days, by mouth). The racemic compound and the [−] 2OHOA isomer produced significant reductions (*P<0.05; **P<0.01) in the plasmatic glucose levels (mg/dL, ordinate axis; n=6).

Figure 9:
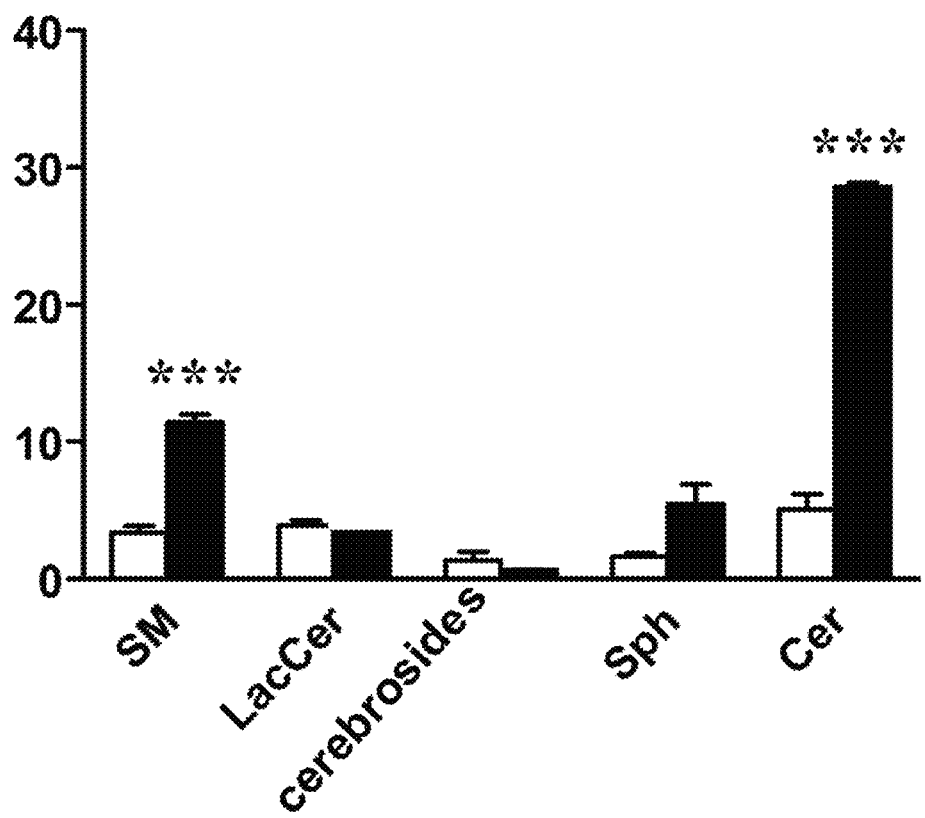

FIG. 9. Regulation of the activity of enzyme 2.3.1.50. The ordinate axis (y) shows the level of incorporation of [$^3$H] palmitate (dpm/mg protein) in different lipid fractions of U118 cells in the absence (control, white bars) or presence of 2OHOA (black bars). A significant increase in radioactivity was found only in the sphingomyelin (SM) and ceramide (Cer) fractions, which clearly indicates selective activation of enzymes EC 2.7.8.27 and 2.3.1.50.

Figure 10:
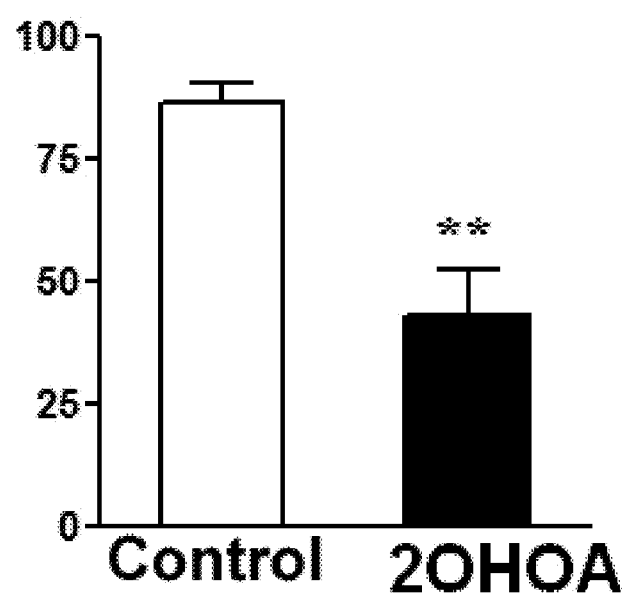

FIG. 10. Regulation of the activity of enzyme 1.14.19.1. The ordinate axis (y) shows the level of incorporation of [$^3$H]oleate (dpm/mg protein) in U118 cell membranes incubated in the absence (control, white bar) or presence of 2OHOA (black bar). The reduction in the incorporation of tritiated oleic in the lipids in the cell membranes incubated in the presence of 2OHOA shows the inhibition of enzyme 1.14.19.1.

DETAILED DESCRIPTION OF THE INVENTION

We will now provide the examples which illustrate the detailed and preferred embodiments of the experiment, without limiting the scope of protection for the invention.

Example 1

Methodology for Obtaining Enantiomers [+] and [−] and Fatty Acid 2-Hydroxiderivate Compounds Racemic Compound Synthesis The following methodology depicts the synthesis of 2-hydroxy fatty acid sodium salts with a 99% of purity, by the creation of the oleic acid dianion by reaction with LDA and later hydroxylation with molecular oxygen; the raw material obtained is treated with NaOH in order to form the sodium salt and is purified by two successive recrystallizations in MeOH/water (avoiding the use of cromatoghafic columns).

With this methodology, is possible to obtain from grams to tons of the final product. The purity of the product can have pharmaceutical quality and be done in "GMP" (Good Manufacturing Practice) conditions, which is required for human consumption.

Scheme

The reaction scheme comprising two steps, hydroxilation and purification, is shown below:

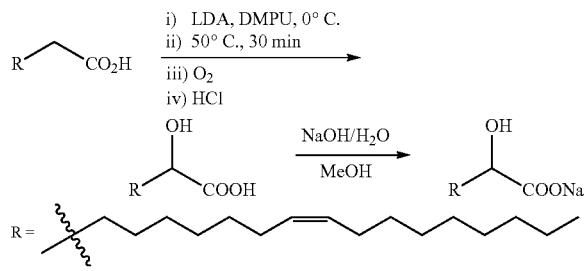

Where R is: —$(CH_2)_a$—$(CH=CH-CH_2)_b$—$(CH_2)_c$—$CH_3$, provided that the total sum of all the carbons in R is equal or higher than 12 or equal or below 18 (for total molecule lengths of between 14 and 20 Carbon atoms).

Process Description

Step 1: Hydroxylation

In a 100 L, enameled and inerted reactor, a diisopropylamine solution (1.7 Kg) in THF (11 L) is cooled below 5° C. N-BuLi (4.6 kg) in portions (23% in hexanes), is added to the solution keeping the temperature below 17° C. After completing the addition, one equivalent of DMPU (1.0 Kg) and an oleic acid solution (2.0 Kg) in THF (2.6 L) are added to the solution, keeping the temperature below 20-25° C. The reaction mixture is heated to 50° C. for 30 minutes and after that is cooled again to 20° C. At this point an $O_2$ cylinder is connected and bubbled during approximately for 45 minutes with a 25 L/min flow. Once the bubbling is completed, the solution is cooled to 10° C. and hydrolysed with HCl 3 M (20 L) to pH=1, keeping the temperature below 40° C. The raw material is extracted in ethyl acetate (6 L), washed with a HCl 3M/brine (1:1) mixture and sodium bisulfite (9 L) and brine (until the pH becomes equal to or below 3) and the solution is concentrated to dryness in a rotary evaporator. Approximately 2 Kg of raw material are obtained with a ≥70% purity.

Step 2: Purification

The raw material is dissolved in 7.2 L of ethanol at 40° C. in a 10 L reactor and is treated with a sodium hydroxide aqueous solution (134 g in 1.4 L of water), increasing the temperature to 50° C. for obtaining an homogeneous solution. It is cooled to 5° C. during at least 6 h for precipitating the sodium salt, which is filtered and washed with acetone. Solid is recrystallized twice in (10%) $H_2O$/MeOH (0.5 L $H_2O$/5.0 L MeOH) at 50° C. to total dilution and cooled for a minimum of 6 h at 0-5° C. The final product is filtered, washed with acetone and dried in vacuum. It is suspended in methanol and the salt formation is completed by adding sodium methoxide. Product is completely precipitated with acetone (5 L) cooling to 0-5° C. during al least 10 h. Solid is filtered, washed with acetone and dried in vacuum.

[+](R) and [−] (S) Enantiomers Production 100 g of the sodium salt of 2OHOA are put in a 1 L reactor and 500 mL of sulphuric acid in ethanol (10% weight) is added. The mix is refluxed for 16 hours and we check that conversion is compete using TLC. When the reaction finishes, it is neutralised using saturated sodium bicarbonate and concentrated in a vacuum to eliminate the ethanol. 250 mL of AcOEt (ethyl acetate) is added to the aqueous emulsion so as to extract the ethyle 2-hydroxyoleate, it is dried on a sulphate and concentrated dry.

100 g of ethyl 2-hydroxioleate (racemic mixture) are put in a 1 L reactor with mechanical agitation in 50 mL of MTBE. 267 mL of tampon phosphate (1 M, pH 7) and 1.3 g of lipase AK *pseudomonas* is added to the solution. The emulsion is shaken at room temperature (25° C.) until 50% conversion is achieved (HPLC, Luna C8, 5 µm, MeOH/water/HCOOH). The reaction is stopped by hydrolysis with HCl 3N until acid pH (less than 2) is reached, it is extracted with MTBE and washed with saline solution until the pH of the waters is 5 or more. The crude is purified by crystalisation to separate the fraction of hydrolysed acid (60% of enantiometric excess) and the fraction of unhydrolysed ester (75% of enantiometric excess).

Each fraction needs two re-processings, repeating the esterification/hydrolysis procedure separately until ee ≥95% is reached for each enantiomer, which is hydrolysed and transformed into the final sodium salt. The final yield of the process is 40-50% (20-25% of each enantiomer).

Methodology Used

The conditions described for the kinetic resolution are the best obtained in the optimisation process, after studying two lipases (one derivate of *Pseudomonas* and another of *Candida Antarctica*), solvents (aqueous, organic or biphasic), temperatures, ionic force, agitation, pH and dilution. We also determined the most appropriate way of monitoring the reaction of the hydrolysis and purification of the products. So, the method for obtaining LP181A1 quiral is different to any found in the bibliography, most of which need high dilutions and purification by chromatography.

Scale Up of the Process

The method was carried out at a scale of 1-150 g obtaining results which were similar and reproducible. The enantiomers can be separated by crystalisation, which facilitates the process on a scale of kg. The decrease in yield is due to manipulation and workup processes. However, no new impurities are generated and the wash waters and crystalisation could be mixed again and reprocessed.

Example 2

Tumoral Cells have Lower Levels of SM in their Membranes, which was Increased after Treatment with the Molecules of the Invention The levels of SM, cultivated in the absence (control) or presence of 200 μM of [−]2OHOA, in normal cell membranes (MRC-5 and IMR90) were measured, and also in several types of tumoral cells (see Table 2). In all cases, we detected that the membranes of tumoral cells have SM levels of about half or a third of that in normal cells (FIG. 1). We can therefore assert that SM concentration is a biomarker which indicates tumorgenesis in human cells. On the other hand, treatments with the molecules of the present invention induce an increase of SM in the tumour cells which is not naturally occurring. So, the SM detection with lysenin and later coupling of a fluorescent anti-body and microscopy detection of confocal fluorescence, showed a more intensive marking (that is to say, a bigger amount of SM) in tumours of animals treated with the molecules of the present invention (FIG. 1c). In an analogous form, other detection methods based in the lysenin bonding with the SM of the membrane and detection by spectroscopic tests in solution or by ELISA showed how the membranes of tumour cells present a greater level of SM only when they are incubated in the presence of molecules of the present invention (FIG. 1). For example, the spectrophotometry determination of solution fluorescence of the SM levels is a very simple, quick and efficient analysis method (FIG. 1D). Thus, this invention has generated a method for diagnosis for detecting the described pathological processes and pathologies in which there are SM level changes, and also for monitoring the efficiency of the therapy using molecules of the present invention and others of similar activity. Based on this knowledge, this invention also includes kits for diagnosing these diseases.

TABLE 2

Effects of [−]2OHOA on levels of sphingomyelin.

| Cell Line | Type of Cancer | % SM before treatment | % SM after treatment | Effect[1] | Techn[2] |
|---|---|---|---|---|---|
| T98G | Glioma (human) | 5 | 19 | + | 4 |
| A172 | Glioma (human) | 8 | 23 | + | 4 |
| U118 | Glioma (human) | 10 | 28 | + | 1, 2, 3, 4, 5 |
| SF767 | Glioma (human) | 5 | 24 | + | 1, 2, 3 |
| U87 | Glioma (human) | 11 | 21 | + | 5 |
| SF268 | Glioma (human) | 12 | 26 | + | 5 |
| 1321N1 | Glioma (human) | 12 | 27 | + | 1 |
| C-6 | Glioma (rat) | 10 | 20 | + | 5 |
| SH-SYSY | Neuroblastoma (human) | 14 | 22 | + | 5 |
| A549 | Luna cancer (human) | 12 | 33 | + | 1, 2, 3 |
| Jurkat | Leukaemia (human) | 12 | 27 | + | 1 |
| U937 | Lymphoma (human) | 12 | 24 | + | 5 |
| HepG2 | Cancer of the liver (human) | 14 | 35 | + | 4 |
| MDA-MB-231 | Breast cancer (human) | 13 | 31 | + | 1 |
| PC3 | Prostate cancer (human) | 12 | 27 | + | 1 |
| BXPC3 | Cancer of the Pancreas (human) | 13 | 26 | + | 4 |
| HeLa | Cancer of the uterus (human) | 9 | 21 | + | 4 |
| HT29 | Cancer of the colon (human) | 11 | 21 | + | 5 |
| IMR90 | Non-tumoral fibroblast (human) | 21 | 23 | − | 1 |
| MRC-5 | Non-tumoral fibroblast (human) | 20 | 24 | − | 1 |

[1] Anti-proliferation effect: + inhibition of cell growth, − absence of effect.
[2] Technique used for the analysis:
1) TLC or HTPLC,
2) gas chromatography,
3) image analysis,
4) fluorescence spectroscopy,
5) confocal or fluorescence microscopy.

Example 3

2OHOA Increases Levels of SM by Activating Enzyme EC 2.7.8.27

Figure 6:
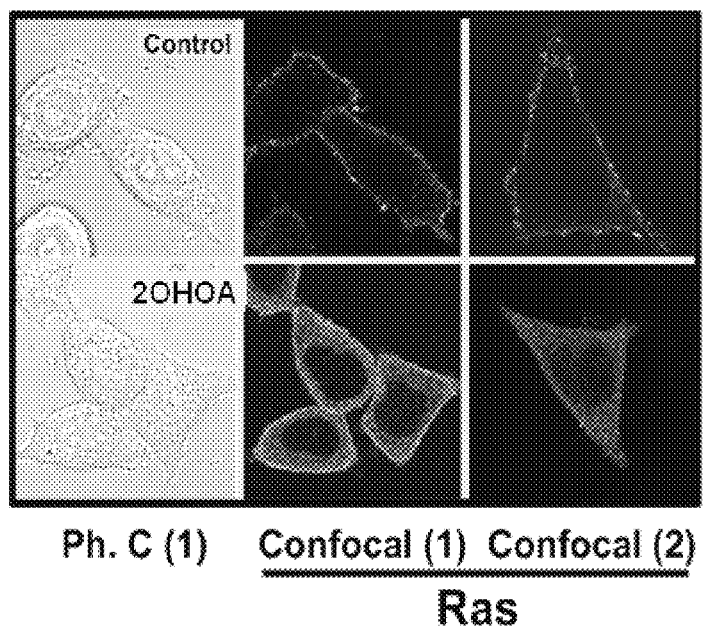
Figure 6:
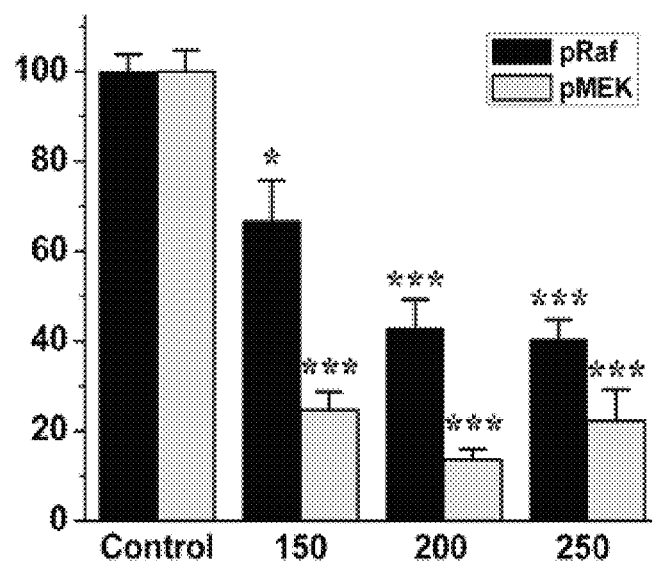
Figure 6:
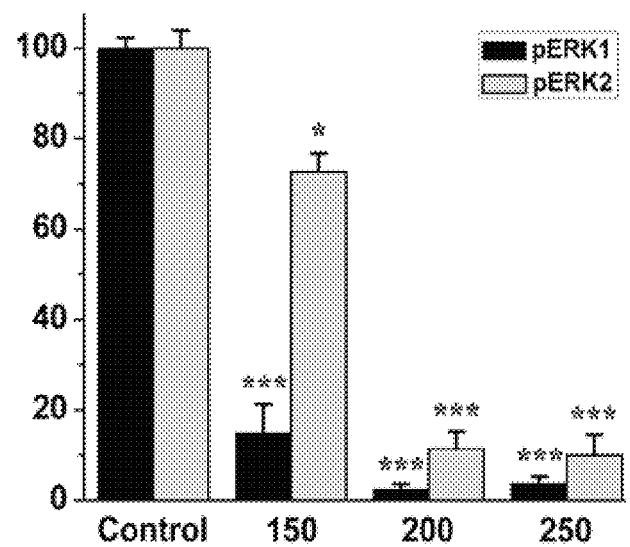
Figure 6:
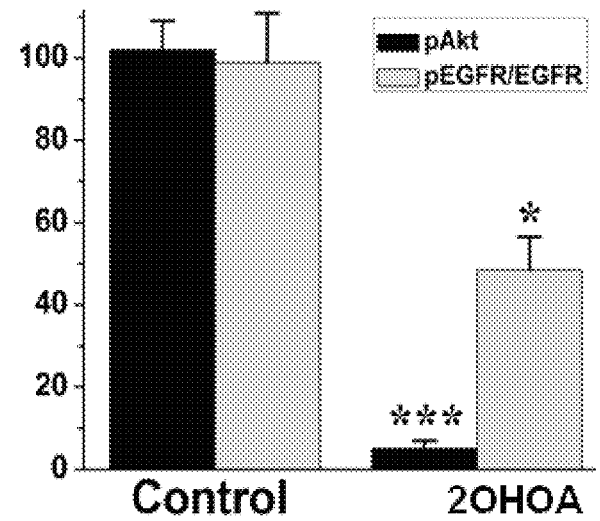
Figure 6:
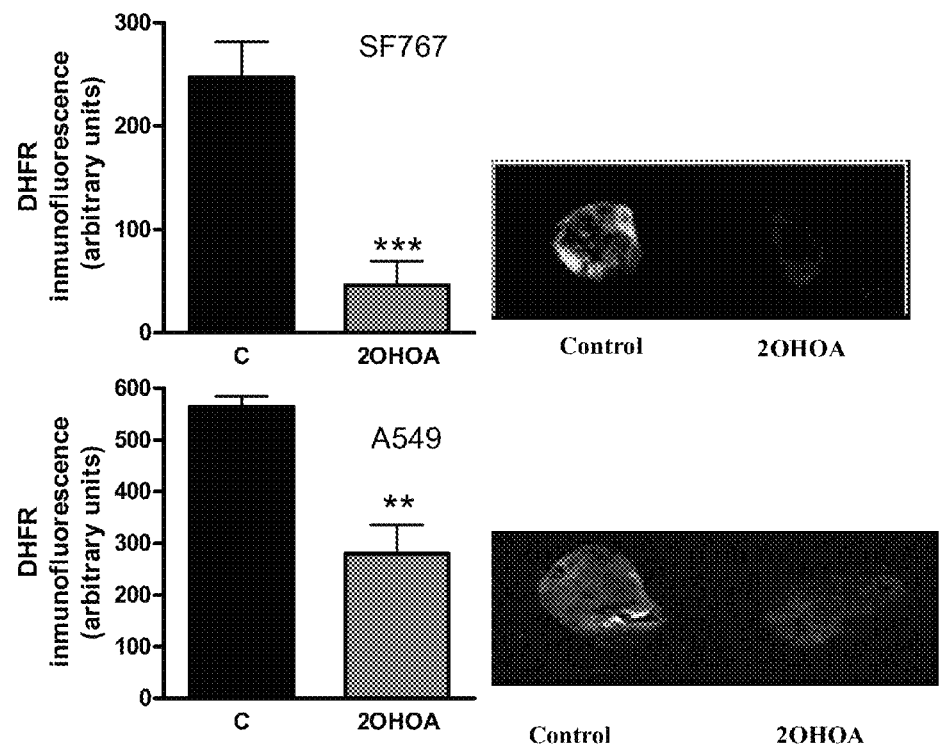
Figure 6:
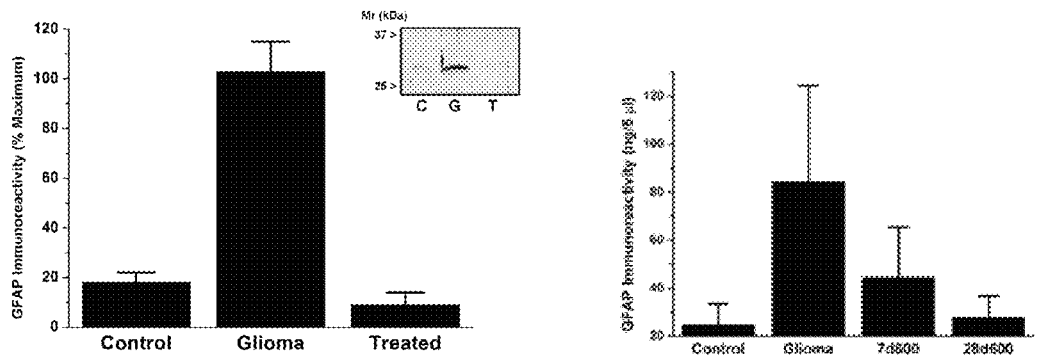

2OHOA increases levels of SM in tumoral cells treated as explained above. Increases of SM in tumoral cells treated with 2OHOA depended on the period of treatment and the concentration used (FIG. 2), which shows the specificity of this molecule. SM is lipid in the membrane which impedes the bonding of certain molecules involved in the proliferation of cells, such as the Ras protein. In this way, levels of Ras were measured by confocal microscopy, using an antibody marked fluorescently, and we were able to detect that the marker passed from the membrane (FIG. 6: 95-99% of total detected fluorescence in the membrane before treatment) to the cytoplasm (94-97% of fluorescence detected in the inside of the cell after treatment with 2OHOA) in human glioma, lung cancer and leukaemia cells. The translocation of Ras from the membrane to the cytoplasm means an absence of productive interaction between Ras and Receptor-Tirosine-Kinase (RTK) or between Ras and Raf, so the proteins in MAP kinase chain are not activated and the tumoral cells cease to proliferate and programmed cell death starts. Changes in cell physiology induced by the molecules of present invention, have as intermediate effects (prior to the cancer cells death or the regulation of the activity in other cells), the induction of dramatic reductions in DHFR levels and dramatic increases of GFAP levels (FIG. 6).

Another effect associated to the reduction in cell proliferation is an increase in the levels of nuclear SM. Treatments with 2OHOA produced increases in the level of nuclear SM (FIG. 3), which shows that it induces inhibition of cell proliferation.

Example 4

Regulation of Enzyme EC 2.7.8.27 Depends on the Molecular Structure of the Fatty Acid In vitro studies using the specific fluorescent substrate of enzyme EC 2.7.8.27, NBD-Cer, show that 2OHOA interacts directly with it, and enzymatic activation is visible from the first few minutes of incubation in the cell cultures (FIG. 4A). The speed of the phenomenon clearly indicates direct and effective interaction between enantiomer 2OHOA and enzyme EC 2.7.8.27. So, this invention refers to the use of the aforementioned compounds as activators (enantiomer [−]), or inhibitors (enantiomer [+]) specific to enzyme EC 2.7.8.27.

On the other hand, activating the enzyme EC 2.7.8.27 depends on the number of carbon atoms in the fatty acid, such that fatty acids of more than 20 carbon atoms do not produce significant changes in the activity of this enzyme (FIG. 5). Furthermore, other requisites for activating enzyme EC 2.7.8.27 are the presence of an OH group in the carbon 2 and one ore more double bonds, as the presence of other radicals (such as H or $CH_3$) and a lack of double bonds in the structure of the fatty acid produced inactive molecules (FIG. 5). SM has a molecular structure which determines the effects on the cellular physiology and which justifies the reversion of different pathological processes. Its voluminous polar head impedes the anchoring of Ras on the membrane via its isoprenyl remains (which prefers regions of the membrane with phospholipids with a small polar head like phosphatdyethanolamine), which in turn impedes later signalling via proteins in the MAP kinases chain. Inactivating this line induces, among other phenomena, a stop in the proliferation of tumoral cells (FIG. 8A and Table 2). Compounds of the present invention have demonstrated being able to regulate in a positive (increases) or negative (reductions) way levels of SM in the cells. Given that membrane composition is critical for its correct operation, both the EC 2.7.8.27 enzyme activators (S or − enantiomers) and their inhibitors (R or + enantiomers) have therapeutic activity, as it has been shown herein. This activation is based in structural principles and follows the structure-function parameters of any other molecule with therapeutic activity.

Example 5

Isomers [−] of Fatty Acids C18 Like [−]2OHOA, are Specific Activators of Enzyme EC 2.7.8.27

The relative structural conformation of hydroxide carbons 1 and 2 (C1 and C2) gives rise to enantiomers or optic isomers [−] (which corresponds with structural conformation S) and [+] (which corresponds with structural conformation R). Thanks to the process described in this invention (Example 1), we have synthesised and isolated the racemic compound whose capacity for regulating both positively and negatively EC 2.7.8.27 enzyme and enantiomers and optical isomers has been proven and measured their capacity for activating enzyme EC 2.7.8.27. FIG. 7A shows activation of said enzyme, measured by levels of SM in human U118 glioma cells after 24 hours in the presence of 50 and 100 mM of each isomer, and also of the racemic mix (which contains more or less the same amount of both). FIG. 7A shows how racemic 2OHOA produces significant increases in SM levels in the cell membrane of U118 cells. At the same time, optic isomer [−]2OHOA (corresponding to optical isomer S) can produce even greater increases in SM levels. Therefore, and in the specific case of this enzyme, the presence of mixtures with a certain percentage of [−]2OHOA (being the racemic compound and special case) behaves as an specific activator of EC 2.7.827. On the other hand, optic isomer [+]2OHOA not only induces increases in SM, but also produces a decrease in the level of SM in membranes. This data indicates that optic isomer [−]2OHOA is a specific activator of enzyme EC 2.7.8.27, and that optic isomer [+]2OHOA is a specific inhibitor of this enzyme. Therefore, this invention protects the use of optic isomer [−]2OHOA (S) as an activator of enzyme EC 2.7.8.27, and of optic isomer [+]2OHOA (R) as a specific inhibitor of this enzyme for therapeutic uses. These results can be extended to all unsaturated fatty acids between 14 and 20 carbon atoms, which present one or more double bonds and a hydroxyl radical in carbon C2(alpha carbon: FIG. 7B).

Example 6

[−] Isomers of Fatty Acids C18, Such as [−]2OHOA, Used as Therapeutic Agents for Treating Human Diseases Enantiomer [−]2OHOA and its derivates shown in this invention have therapeutic applications in different fields, such as treating cancer, obesity, cardiovascular pathologies, diabetes, metabolic syndrome, medullar injuries, Alzheimer's disease and other processes (FIGS. 6 and 8; Tables 2-5). On the other hand, enantiomer [+]2OHOA has a positive effect on cholesterol and triglyceride levels, since it induced significant reductions in plasmatic levels of these lipids, whose high levels are considered as negative for human health (FIG. 8). Therefore, the therapeutic effects of each isomer were studied, and also the racemic mixture, in different pathological models.

FIG. 8A shows the effect of oral treatments (15 days, 600 mg/kg daily, n=6) with racemic 2OHOA and enantiomers [−]2OHOA and [+]2OHOA, on the volume of tumours derived from human lung cancer (cells A549) in naked mice. As can be seen, the effect of optic isomer [−]2OHOA is greater than the racemic. On the other hand, after 15 days of treatment with optic isomer [+]2OHOA, there were no significant changes in the volume of tumours. This shows that isomer [−]2OHOA is the one that activates enzyme EC 2.7.8.27 and has therapeutic antitumoral effects. On the other hand, we investigated the antitumoral activity of these compounds in different types of human cancer (see Tables 2, 4 and 5). At this respect, all the enantiomers [−] of the present invention showed more potency than the racemic and the enantiomer [+] in cancer treatment, which corresponds with significantly lower levels in the IC50 for inhibiting the growth of human lung cancer (Line A549). Furthermore, the activity of these enantiomers was proven against a vast variety of human cancers of different nature, since it can be stated that enantiomers [−] of 2-hydroxylated fatty acids have a high potency in the treatment of any type of cancer. This potency proved to be somehow even higher for salts (mainly the sodium salt of these molecules) than for the free fatty acid (results not shown). In any case, enantiomers [−] both in acid and salt form, always showed a greater potency than any of the alternative molecular forms in inhibiting tumour growth.

What is more, we studied the effect of the isomers above on arterial pressure, body weight, and the level of cholesterol, triglycerides and glycemia (glucose in plasma) in SHR rats SHR (FIGS. 8B, 8C and 8D and 8E). Analogous to the above, there was a greater therapeutic effect in the control of blood pressure, corporal weight and glycemia when isomer [—]2OHOA was used, while enantiomer [+]2OHOA had a greater therapeutic effect in the treatment of hypercholesterolemia, hypertriglyceridemia. Thus, animals treated with isomer [—]2OHOA showed reductions in systolic pressure greater than 7998 Pa (60 mm Hg), while those treated with isomer [+]2OHOA and with the racemic product had a considerable therapeutic effect but of lower amplitude. Similarly, during 1 and 5 days of treatment, rats treated with the racemic loosed 11 gram of weight (approximately a 3% of their body weight), whereas animals of the group treated with enantiomer [−]2OHOA loosed 21 grams and animals of the group treated with enantiomer [+]2OHOA only loosed 7 grams of weight. On the other hand, a higher effect of enantiomer [+]2OHOA in the reduction of triglyceride (TG) and total cholesterol (CHOt) levels was observed (FIG. 8D) At this respect, plasmatic basal levels of TG in SHR rats are of 108 mg/dl and were reduced to 56 mg/dl after 2 weeks treatment with enantiomer [+]2OHOA. On the other hand, treatment with enantiomer [+]2OHOA inducted a reduction of plasmatic TG levels to 47 mg/dl, whereas enantiomer [−]2OHOA only produced a modest reduction to 81 mg/dl. In parallel, levels of CHOt were reduced from 73 mg/dl to 43 mg/dl (racemic), 36 mg/dl (enantiomer [+]2OHOA) and 59 mg/dl (enantiomer [−]2OHOA), respectively. Finally, treatment with the enantiomers of the present invention also produced significant reductions in plasma glucose levels (FIG. 8E). In this case, both the racemic (2OHOA) and the enantiomer [−]2OHOA inducted significant reductions in rat's glycemias (P<0.05 and P<0.01), respectively: FIG. 8E). Nevertheless, enantiomer R([+]2OHOA) inducted a reduction without statistical significance.

For all the above, this invention proves that optic isomers [+] [−] of unsaturated hydroxide acids of 18 carbone atoms are efficient molecules and with therapeutic activity for the treatment of abovementioned pathologies. In all studied cases, one and only one of the enantiomers showed to have an activity higher to those of the other molecular forms (statistical significance always P<0.05). Thus, enantiomer [−] showed to be more efficient in curing cancer, obesity, diabetes, hypertension, etc., whereas enantiomer [+] showed to be more efficient in controlling the hypercholesterolemia and hypertriglyceridemia. In these cases, the racemic compound showed as an intermediate situation, capable of emulating the positive effects of each one of the optical isomers, but with lower potency, due to the lower concentration of the active enantiomer in each case. Furthermore, the use of the inaccurate enantiomer induced undesired side effects which were avoided at therapeutic doses of the most active enantiomer (Table 3).

Example 7

Efficiency, Toxicity and Side Effects of the Enantiomers in this Invention

This example recounts the study carried out on immunodepressed mice infected with human glioma (SF767) cells and treated for 15 days (orally) with the indicated dose (Table 3). This table shows the volume of tumours at the end of treatment and symptoms observed during the days treatment lasted. We should note, once more, that the efficiency of enantiomer [−]2OHOA is greater than that of racemic compound 2OHOA, and that enantiomer [+]2OHOA showed no activity after 15 days of treatment with the indicated dose.

On the other hand, the dose which induced reductions of about a third of the volume of tumours had no side effects in animals treated with [−]2OHOA (50 mg/kg), whereas animals treated with racemic compound 2OHOA at a dose which induced a similar decrease in the volume of tumours (600 mg/kg) showed important side effects (Table 3). Furthermore, at 200 mg/kg, enantiomer [−]2OHOA induced an 89% decrease in the volume of the tumour, whereas the racemic compound only induced reductions of 23% in the volume of tumours and some animals showed adverse side affects to the treatment.

From these findings we can deduce that enantiomer [−]2OHOA has greater potency and that at maximum therapeutic dosage has no adverse side effects, whereas the racemic compound has less effect and produces certain unwanted side effects at therapeutic doses. The differences in efficiency in treating tumoral processes between enantiomer [−]2OHOA and the racemic may mean months or years in the life expectancy of patients. Furthermore, the differences in efficiency can mean curing a particular cancer in a patient or not. On the other hand, the differences in toxicity at therapeutic doses may mean a greater quality of life for patients who take the enantiometric form of [−]2OHOA. Given that the activation mechanism of the compound is linked to enzyme EC 2.7.8.27 and that enantiomers [−] and [+] have opposing effects on said enzyme (FIG. 7), that administering the racemic compound involves the presence of a molecular form which has the opposite effect to that of the active principle ([−]2OHOA), reversing part of the therapeutic effect of the latter.

TABLE 3

| Dose | 2OHOA | | [−]2OHOA | | [+]2OHOA | |
|---|---|---|---|---|---|---|
| mg/kg | Effect[1] | Toxicity[2] | Effect[1] | Toxicity[2] | Effect[1] | Toxicity[2] |
| 50 | +2% | No | −35% | No | −2% | No |
| 75 | −7% | No | −54% | No | +7% | No |
| 100 | −8% | No | −65% | No | −3% | No |
| 150 | −17% | No | −78% | No | +1% | No |
| 200 | −23% | Diarrhoea 16% Behaviour 16% | −89% | No | −4% | Diarrhoea 16% Behaviour 16% |
| 400 | −39% | Diarrhoea 32% Behaviour 16% | −91% | Diarrhoea 16% Behaviour 16% | −2% | Diarrhoea 16% Behaviour 32% |
| 600 | −37% | Diarrhoea 50% Behaviour 50% | −86% | Diarrhoea 32% Behaviour 50% | +3% | Diarrhoea 66% Behaviour 50% |

[1]Variation in the size of the tumour after 15 days treatment (orally) at the dose indicated, compared with untreated animals (n = 6 in all the groups). In this case, the value 100% was assigned to the volume of the tumour of control animals (treated with vehicle) upon the conclusion of the 15 days treatment.
[2]Symptoms registered and percentage of animals in which they were observed. The symptoms in behaviour include decreased mobility for at least 30 minutes, hair standing on end, jumping, or staying in a corner of the cage.

Studies performed with the racemic and enantiomer compounds of the present invention prove that, in all cases, enantiomer [−] has a higher potency against tumours than the other molecular forms for inhibiting the growth of human cancer cells (A459, Table 4). At this respect, concentrations which inhibit growth of tumour cells ($IC_{50}$) are lower for the enantiomer S ([−]) in all studied tumour lines (Table 5). On the contrary, these compounds did not induce the death of normal cells (MRC-5, IMR90). In all of the cases, the molecules employed were in the form of sodium salt.

TABLE 4

Effect of invention compounds in the growth of lung cancer human cells, A549

| | $IC_{50}$ (µM) | | |
|---|---|---|---|
| | Racemic | [−] | [+] |
| 2OH16:1 | 192.7 ± 9.3 | 110.2 ± 14.0*§§§ | 299.0 ± 34.2* |
| 2OH18:1 | 94.1 ± 8.8 | 52.6 ± 9.5**§§§ | 133.3 ± 9.8* |
| 2OH18:2 | 105.0 ± 4.1 | 69.9 ± 11.2*§§§ | 186.3 ± 21.9* |
| 2OH18:3a | 219.2 ± 15.4 | 146.1 ± 10.9*§§§ | 351.4 ± 22.7** |
| 2OH18:3g | 206.5 ± 21.7 | 155 ± 7.5*§§§ | 341.8 ± 31.5** |

*P < 0.05;
**P < 0.01: significantly different from the racemic;
§§§P < 0.001 with respect to enantiomer [+].

Example 8

Regulating the Compounds in this Invention on the Activity of Enzyme EC 2.3.1.50

We incubated human glioma cells U118 in the presence or absence (control) of 2OHOA (200 mM, 24 h) and later incubated them with [$^3$H]palmitate for 5 minutes. After these periods of incubation, we extracted the cellular lipids and separated them by TLC. The bands correspond to each species of lipid extracted and the amount of radioactive palmitate incorporated was measured by liquid shining. As we can see, not only was there an important incorporation of the fraction of the SM (an indicator of the activity of enzyme EC 2.7.8.27), but also in the fraction of the ceramide, which indicates activity of enzyme EC 2.3.1.50 (serin-palmitoil transferase). Therefore, we can conclude that 2OHOA is a specific activator of enzyme EC 2.3.1.50 (FIG. 9).

TABLE 5

Effect of racemic 2OHOA and its enantiomers on the growth of several lines of different types of human cancers. $IC_{50}$ Values (µM).

| Cellular Line | Cancer Type | Racemic 2OHOA | [−]2OHOA | [+]2OHOA |
|---|---|---|---|---|
| U118 | Glioma (human) | 142.3 | 97.8 | 211.6 |
| SF767 | Glioma (human) | 214.8 | 102.1 | 304.1 |
| U87 | Glioma (human) | 81.6 | 53.5 | 148.3 |
| SH-SY5Y | Neuroblastoma (human) | 119.1 | 64.4 | 193.4 |
| A549 | Lung Cancer (human) | 94.1 | 52.6 | 133.3 |
| Jurkat | Leukemia (human) | 62.9 | 35.7 | 97.2 |
| U937 | lymphoma (human) | 183.2 | 136.3 | 213.5 |
| HepG2 | Liver Cancer (human) | 41.4 | 32.9 | 76.7 |
| MDA-MB-231 | Breast Cancer (human) | 243.7 | 145.2 | 328.0 |
| PC3 | Prostate Cancer (human) | 137.5 | 87.0 | 232.8 |
| BXPC3 | Pancreas Cancer (human) | 98.3 | 61.8 | 154.1 |
| HeLa | Uterus Cancer (human) | 126.8 | 74.5 | 205.7 |
| HT29 | Colon Cancer (human) | 224.6 | 159.4 | 341.6 |
| A375 | Malignant Melanoma (human) | 272.9 | 163.1 | 407.3 |
| IMR90 | Non tumor Fibroblast (human) | >5,000 | >5,000 | >5,000 |
| MRC-5 | Non tumor Fibroblast (human) | >5,000 | >5,000 | >5,000 |

Example 9

Regulating the Compounds of this Invention on the Activity of Enzyme EC 1.14.19.1

Oleic acid is synthesised from esteric acid by the activity of the estearoil-CoA desaturase enzyme (EC 1.14.19.1). This enzyme is crucial in lipid metabolism, as it is a limitant in the synthesis of fatty acids. To see whether this reduction was due to regulation of enzyme EC 1.14.19.1, we incubated U118 cells in the presence or absence of 2OHOA (200 µM, 24 h) and, later, in the presence of [$^3$H]oleate (5 minutes). We were able to observe that the incorporation of radioactive oleic acid in U118 cell membranes incubated in the presence of 2OHOA was significantly less than in control cells (FIG. 10). This result indicates that 2OHOA is a powerful inhibitor of enzyme EC 1.14.19.1, whose regulation has been proposed as important for the treatment of several human pathologies.

REFERENCES

1. Albi, E. and M. V. Magni (1999). Sphingomyelin synthase in rat liver nuclear membrane and chromatin. FEBS Lett 460: 369-72.
2. Alemany R, Terés S, Baamonde C, Benet M, Vögler O, Escribá P V. (2004) 2-hydroxyoleic acid: a new hypotensive molecule. *Hypertension.* 43: 249-54.
3. Alemany R, Perona J S, Sánchez-Domínguez J M, Montero E, Cañizares J, Brezan R, Escribá P V and Ruiz-Gutiérrez V (2007) G protein-coupled receptor systems and their lipid environment in health disorders during aging. *BBA Biomembr.* 1768:964-975.
4. Buda C, Dey I, Balogh N, Horvath L I, Maderspach K, Juhasz M, Yeo Y K, Farkas T (1994) Structural order of membranes and composition of phospholipids in fish brain cells during thermal acclimatization. *Proc. Natl. Acad. Sci USA* 91:8234-8238.
5. Escriba P V, Sastre M, Garcia-Sevilla J A. (1995) Disruption of cellular signaling pathways by daunomycin through destabilization of nonlamellar membrane structures. Proc Natl Acad Sci USA. 92:7595-7599.
6. Escriba P V, Ozaita A, Ribas C, Miralles A, Fodor E, Farkas T, Garcia-Sevilla J A (1997) Role of lipid polymorphism in G protein-membrane interactions: nonlamellar-prone phospholipids and peripheral protein binding to membranes. Proc Natl Acad Sci USA. 94:11375-11380.
7. Escribá P V (2006) Membrane-lipid therapy: a new approach in molecular medicine. *Trends Mol. Med.* 12:34-43
8. Escribá P V, González-Ros J M, Goñi F M, Kinnunen P K J, Vigh L, Sánchez-Magraner L, Fernández A M, Busquets X, Horváth I, Barceló-Coblijn G (2008) Membranes: A meeting point for lipids, proteins and therapies. *J. Cell. Mol. Med.* 12:829-875.
9. Florent S, Malaplate-Armand C, Youssef I, Kriem B, Koziel V, Escanyé M C, Fifre A, Sponne I, Leininger-Muller B, Olivier J L, Pillot T, Oster T. (2006) Docosahexanoic acid prevents neuronal apoptosis induced by soluble amyloid-beta oligomers. *J Neurochem.* 96:385-95.
10. Huitema, K., et al. (2004). Identification of a family of animal sphingomyelin synthases. EMBO J 23:33-44.
11. Jackson C L, Schwartz S M (1992) Pharmacology of smooth muscle cell replication. *Hypertension* 20: 713-716.
12. Jiang Q, et al. (2011). Gamma-tocotrienol induces apoptosis and autophagy in prostate cancer cells by increasing intracellular dihydrosphingosine and dihydroceramide. Int J. Cancer. doi: 10.1002/ijc.26054.
13. Jung U J, Torrejon C, Tighe A P, Deckelbaum R J. (2008). N-3 Fatty acids and cardiovascular disease mechanisms underlying beneficial effects. *Am J Clin Nutr.* 87:2003 S-2009S.
14. Lane R M, Farlow M R. (2005) Lipid homeostasis and apolipoprotein E in the development and progression of Alzheimer's disease. *J Lipid Res.* 46: 949-968.
15. Lladó V, Gutiérrez A, Martínez J, et al. Minerval induces apoptosis in Jurkat and other cancer cells. J. Cell Mol Med. 2010; 13: 1-12.
16. Martínez J, O, Casas J, F, Alemany R, Prades J, Nagy T, Baamonde C, Kasprzyk P, Terés S, Saus C, Escribá P V. (2005) Membrane structure modulation, protein kinase C alpha activation, and anticancer activity of minerval. Mol Pharmacol 67:531-40.
17. Perona J S, Vögler O, Sánchez-Domínguez J M, Montero E, Escribá P V and Ruiz-Gutiérrez E V (2007) Consumption of virgin olive oil influences membrane lipid composition and regulates intracellular signaling in elderly adults with type 2 diabetes mellitus. *J Gerontol A Biol Sci Med Sci* 62: 256-263.
18. Sagin F G, Sozmen E Y (2008) Lipids as key players in Alzheimer disease: alterations in metabolism and genetics. *Curr Alzheimer Res* 5:4-14.
19. Simons, K. and D. Toomre (2000). Lipid rafts and signal transduction. Nat Rev Mol Cell Biol 1:31-9.
20. Sloan, F. A., Bethel, M. A, Ruiz, D. Jr., Shea, A. M & Feinglos, M. N. The growing burden of diabetes mellitus in the US elderly population. Arch. Intern. Med. 168, 192-199 (2008).
21. Slomiany A, Murty V L, Aono M, Snyder C E, Herp A and Slomiany B L (1982) Lipid composition of tracheobronchial secretions from normal individuals and patients with cystic fibrosis. *Biochim Biophys Acta.* 10:106-111 D.
22. Stender S, Dyerberg J (2004) Influence of trans fatty acids on health. *Ann. Nutr. Metab.* 48:61-66.
23. Schwartz S M, Campbell G R, Campbell J H. (1985). Replication of smooth muscle cells in vascular disease. *Circ Res* 58:427-444.
24. Tafesse, F. G., P. Ternes, et al. (2006). The multigenic sphingomyelin synthase family. *J Biol Chem* 281(: 29421-5.
25. Trombetta A, Maggiora M, Martinasso G, Cotogni P, Canuto R A, Muzio G. (2007). Arachidonic and docosahexanoic acids reduce the growth of A549 human lung tumor cells increasing lipid peroxidation and PPARs. *Chem Biol Interact.* 165:239-50.
26. Van Helvoort, A., W. van't H of, et al. (1994). Conversion of diacylglycerol to phosphatidylcholine on the basolateral surface of epithelial (Madin-Darby canine kidney) cells. Evidence for the reverse action of a sphingomyelin synthase. J Biol Chem 269: 1763-9.
27. Vögler O, Casas J, Capó D, Nagy T, Borchert G, Martorell G and Escribá P V. (2004) The G betagamma dimer drives the interaction of heterotrimeric Gi proteins with non-lamellar membrane structures. *J Biol Chem.* 279:36540-36545.
28. Vögler O, López-Bellan A, Alemany R, Tofé S, González M, Quevedo J, Pereg V, BarcelóF and Escribá P V. (2008) Structure-effect relation of C18 long-chain fatty acids in the reduction of body weight in rats. *Int J Obes.* 32: 464-473.
29. Wise L E, Iredale P A, Stokes R J, Litchman A H (2007) Combination of Rimonabant and Donepezil prolongs spatial memory duration. *Neuropsychopharmacology* 32: 1805-1812.
30. Yang, Q, Alemany, R, Casas, J, Kitajka, K, Lanier, S M, Escribá P V (2005) Influence of the membrane lipid structure on signal processing via G protein-coupled receptors. Mol Pharmacol 68:210-7.

The invention claimed is:
1. An enantiomer [−] of a compound of Formula I:

$$\text{HOOC—HOCH—(CH2)}_a\text{-(CH=CH—CH2)}_b\text{-(CH2)}_c\text{-CH3} \quad (I)$$

or its pharmaceutically acceptable salts, resulting from the selection from at least one of the following combinations of a, b and c values:
a=6, b=1 and c=4
a=6, b=1 and c=6 a=6, b=2 and c=3
a=6, b=3 and c=0
a=3, b=3 and c=3.

2. The enantiomer, according to claim 1, characterized by the formula: [−]HOOC—HOCH—$(CH_2)_6$—(CH═CH—$CH_2)_1$—$(CH_2)_6$—$CH_3$ or its pharmaceutically acceptable salts.

3. The enantiomer, according to claim 1, characterized in that the pharmaceutically acceptable salt is a sodium salt.

4. A pharmaceutical composition comprising at least one enantiomer according to claim 1 and/or at least one of its pharmaceutically acceptable salts, and optionally, any pharmaceutically acceptable vehicle.

5. An in vitro method for the treatment of pathologies whose common etiology is an abnormally low sphingomyelin level, and/or an abnormally low Glial Fibrillary Acidic Protein (GFAP) level and/or an abnormally high Dihydrofolate Reductase (DHFR) level, said method comprising administration to the patient of a therapeutically effective amount of an enantiomer of claim 1 or a composition that contains it.

6. The method of claim 5, wherein the enantiomer is [−]HOOC—HOCH—$(CH_2)_6$—(CH═CH—$CH_2)_1$—$(CH_2)_6$—$CH_3$ or its pharmaceutically acceptable salts.

7. The method of claim 5, wherein the pathology treated is selected from the group consisting of cancer, vascular pathologies, and metabolic pathologies.

8. The method of claim 5, wherein the cancer is selected from the group consisting of liver cancer, melanoma, prostate cancer, breast cancer, pancreatic cancer, leukemia, cervix cancer, colon cancer, brain cancer, and lung cancer.

9. The method of claim 5, wherein the vascular pathology is selected from the group consisting of hypertension, atherosclerosis, cardiomyopathies, angiogenesis, and cardiac hyperplasia.

10. The method of claim 5, wherein the metabolic pathology is selected from the group consisting of diabetes, metabolic syndrome, and obesity.

* * * * *